(12) United States Patent
Arakawa et al.

(10) Patent No.: US 9,355,826 B2
(45) Date of Patent: May 31, 2016

(54) METHOD FOR IMAGING MASS ANALYSIS USING PHYSICAL VAPOR DEPOSITION OF PLATINUM NANOPARTICLES

(71) Applicants: A SCHOOL CORPORATION KANSAI UNIVERSITY, Suita-shi, Osaka (JP); NISSAN CHEMICAL INDUSTRIES, LTD., Tokyo (JP)

(72) Inventors: Ryuichi Arakawa, Suita (JP); Hideya Kawasaki, Suita (JP); Tomoyuki Ozawa, Funabashi (JP)

(73) Assignees: A SCHOOL CORPORATION KANSAI UNIVERSITY, Suita-shi, Osaka (JP); NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/379,228

(22) PCT Filed: Feb. 13, 2013

(86) PCT No.: PCT/JP2013/053743
§ 371 (c)(1),
(2) Date: Aug. 15, 2014

(87) PCT Pub. No.: WO2013/122225
PCT Pub. Date: Aug. 22, 2013

(65) Prior Publication Data
US 2015/0021470 A1    Jan. 22, 2015

(30) Foreign Application Priority Data
Feb. 17, 2012    (JP) ................................ 2012-033258

(51) Int. Cl.
*H01J 49/26*    (2006.01)
*H01J 49/00*    (2006.01)
(Continued)

(52) U.S. Cl.
CPC ............. *H01J 49/0004* (2013.01); *A01N 25/00* (2013.01); *A01N 47/40* (2013.01);
(Continued)

(58) Field of Classification Search
USPC .......................................... 250/281, 282, 288
See application file for complete search history.

(56) References Cited

U.S. PATENT DOCUMENTS

2007/0202304 A1* 8/2007 Golovko .............. B01J 13/0043
428/195.1

FOREIGN PATENT DOCUMENTS

| JP | 2007-157353 A | 6/2007 |
| JP | 2007-309860 A | 11/2007 |

(Continued)

OTHER PUBLICATIONS

Kawasaki et al., Platinum Nanoflowers for Surface-Assisted Laser Desorption/Ionization Mass Spectrometry of Biomolecules, J. Phys. Chem. C 2007, 111, 1627-16283.*

(Continued)

*Primary Examiner* — Nicole Ippolito
(74) *Attorney, Agent, or Firm* — Westerman, Hattori, Daniels & Adrian, LLP

(57) ABSTRACT

The present invention provides an improved method for imaging mass spectrometry using an ionization-assisting matrix of a test sample, wherein the ionization efficiency is high, migration and visual information reduction are inhibited, no interference peaks originating from the matrix occur, and the analysis can be performed at high spatial resolution. Specifically, the present invention provides a method for imaging mass spectrometry using a sample prepared by physical vapor depositing platinum nanoparticles on the surface of a test sample to be subjected to imaging mass spectrometry.

9 Claims, 24 Drawing Sheets

(51) Int. Cl.
*B82Y 30/00* (2011.01)
*A01N 25/00* (2006.01)
*A01N 47/40* (2006.01)
*G01N 1/28* (2006.01)
*B82Y 40/00* (2011.01)

(52) U.S. Cl.
CPC ............... *B82Y 30/00* (2013.01); *G01N 1/28* (2013.01); *H01J 49/26* (2013.01); *B82Y 40/00* (2013.01); *G01N 1/2853* (2013.01)

(56) References Cited

FOREIGN PATENT DOCUMENTS

| JP | 2008-204654 A | 9/2008 |
| JP | 2008-232842 A | 10/2008 |
| JP | 2009-42206 A | 2/2009 |
| WO | 2009/069816 A1 | 6/2009 |

OTHER PUBLICATIONS

Kawasaki et al., "Platinum vapor deposition surface-assisted laser desorption/ionization for imaging mass spectrometry of small molecules", Rapid Communications in Mass Spectrometry, Aug. 30, 2012, vol. 26, No. 16, pp. 1849-1858.

Kawasaki et al., "Platinum Nanoflowers for Surface-Assisted Laser Desorption/Ionization Mass Spectrometry of Biomolecules", Journal of Physical Chemistry, vol. 111, No. 44, 2007, pp. 16278-16283.

Naito, "Mass Microprobe Aimed at Biological Samples", Journal of the Mass Spectrometry Society of Japan, vol. 53, No. 3, 2005, pp. 125-132.

Ozawa et al., "Pt Jochaku ni yoru SALDI/MS Imaging o Mochiita Yuki Zairyo no Bunpu Kaiseki", Kobunshi Bunseki Kenkyu Kondankai, Oct. 25, 2012, pp. 119-120.

Sugiura et al., "Imaging Mass Spectrometry for Visualization of Drug and Endogenous Metabolite Distribution: Toward In Situ Pharmacometabolomes", Journal of Neuroimmune Pharmacology, vol. 5, No. 1, 2010, pp. 31-43.

Sugiura et al., "Two-Step Matrix Application Technique to Improve Ionization Efficiency for Matrix-Assisted Laser Desorption/Ionization in Imaging Mass Spectrometry" Analytical Chemistry, vol. 78, No. 2006, pp. 8227-8235.

Svatos, "Mass spectrometric imaging of small molecules", Trends in Biotechnology, vol. 28, No. 8, 2005, pp. 425-434.

Tang et al., "Gold Nanoparticles and Imaging Mass Spectrometry: Double Imaging of Latent Fingerprints", Analytical Chemistry, vol. 82, No. 5, 2010, pp. 1589-1593.

Yonezawa et al., "Detailed Investigation on the Possibility of Nanoparticles of Various Metal Elements for Surface-Assisted Laser Desorption/Ionization Mass Spectrometry", Analytical Sciences, vol. 25, No. 3, Mar. 2009, pp. 339-346.

International Search Report dated Apr. 2, 2013 issued in corresponding application No. PCT/JP2013/053743.

\* cited by examiner (a)

(b)

(c)

m/z=1111   m/z=1135   m/z=1187

(a)

Photo after platinum vapor deposition
Printing interval 2 mm (b)

Distribution in magenta region
Lost in UV-irradiated region

Distribution of magenta in UV-irradiated region
⇒ Possibility of material decomposed by UV irradiation Distribution in magenta region
Material not lost in UV-irradiated region Platinum vapor deposition Organic matrix (DHB)

Chemical Formula: C₄H₁₀NO₃PS
Molecular Weight: 183.17

Acephate

Acetamiprid

Acetamiprid      Thiophanate methyl

Acephate

★: Sodium adduct (*m/z*=206)

●: Potassium adduct (*m/z*=222)

Chemical Formula: C₄H₁₀NNaO₃PS⁺
Molecular Weight: 206.16

Acephate

US 9,355,826 B2

METHOD FOR IMAGING MASS ANALYSIS USING PHYSICAL VAPOR DEPOSITION OF PLATINUM NANOPARTICLES

TECHNICAL FIELD

The present invention relates to a method for imaging mass spectrometry using physical vapor deposition of platinum nanoparticles.

Specifically, the present invention relates to a method for preparing a sample, comprising physical vapor depositing platinum nanoparticles as an ionization-assisting matrix on the surface of a test sample to be subjected to imaging mass spectrometry, and a method for imaging mass spectrometry using the sample.

BACKGROUND ART

In the fields of biochemistry, medical science, genomic drug discovery, etc., there is a strong demand for analyzing the structures of proteins, etc., in biological tissues and cells. One of the analyzing means for responding to this demand is mass spectrometry. In mass spectrometry, a test sample is irradiated with a laser to ionize biological molecules, etc., in the test sample, and the mass of the generated ions is analyzed (NPL 1).

Elucidating the localization of a target material in a biological tissue has great value in the fields of searching for abnormal materials, tracking pharmacokinetics, etc., in disease. Mass spectrometry is one of the methods of directly discovering and identifying a target material, and imaging mass spectrometry (IMS) has recently been suggested in which a target material in a biological tissue is identified in two dimensions, and the localization is elucidated (PTL 1 to 4, NPL 2 and 3, etc.).

When the distribution of a material in a biological tissue can be visualized and identified in two dimensions, information in vivo, e.g., identification of lesion sites and elucidation of disease-related materials (including intermediates), can be directly obtained, making significant contributions to society. Also, in the field of materials and nanotechnology, which has become increasingly sophisticated in recent years, analyzing the distribution and localization state of materials that help to increase functionality largely affects the expression of properties, production conditions, degradation state, etc. Thus, information obtained by IMS is extremely useful.

To perform mass spectrometry, a test sample needs to be ionized. Known methods of ionization include the use of ionization-assisting agent (matrix)-free secondary ion mass spectrometry (SIMS), and matrix assisted laser desorption/ionization (MALDI), which is capable of analyzing polymers by using a matrix.

These ionization methods are used in conventional IMS; however, the mass range that can be analyzed by SIMS is merely a mass-to-charge ratio (m/z) up to about 1,000. Moreover, most of the test sample is broken (by so-called fragmentation) in the ionization process, and when the test sample is a mixture, the spectra become complicated, making the analysis difficult. For this reason, the ionization method used in IMS is typically MALDI, in which test sample fragmentation rarely occurs; however, IMS using known MALDI has the following problem.

In the known MALDI, chemical synthesis materials (organic matrixes) and materials (inorganic matrixes) in which metal oxides or metal nanoparticles are dispersed in a solvent are known as an ionization-assisting matrix. Examples of organic matrixes include 1,8-dihydroxy-9(10H)-anthracenone (Dithranol), 2-(4-hydroxy phenylazo)benzoic acid (HABA), 2,5-dihydroxybenzoic acid (DHB), $\alpha$-cyano-4-hydroxycinnamic acid (CHCA), sinapinic acid (SA), etc., and the organic matrix is selected and used according to the analysis material (proteins, peptides, synthetic polymers, etc.).

In all conventional IMS, known organic matrixes for MALDI are used. However, since these organic matrixes were not originally developed for IMS, although the ionization efficiency is high, the matrix ability is reduced or lost in the presence of salt. Thus, these organic matrixes are not suitable for IMS that analyzes a crude test sample such as a salt-containing biological tissue. Further, since strong ion peaks originating from an organic matrix occur in a low molecular weight range (m/z: 700 or less), precise analysis is difficult when a target material is a drug, additive, etc., having a low molecular weight.

When a known organic matrix is used in INS, the matrix is added dropwise or injected in a liquid (solution) state to a test sample to incorporate an analysis subject. A crystal particle containing the analysis subject is then formed after drying. The crystal particle of the matrix obtained herein typically has a size of about 50 $\mu$m or more (NPL 4). Since the analysis subject is dispersed in the crystal particle of the matrix, even when the laser beam irradiation diameter for ionization is reduced, spatial resolution higher than the crystal particle size of the matrix cannot be obtained.

Further, when a liquid matrix is adhered to a test sample, the used liquid causes physical movement (so-called migration) of a target material, which causes the distribution information of the analysis subject to be lost. Moreover, the adhesion of a liquid matrix to a test sample allows crystal particles to cover tissue, which causes visual information to be lost, making identification of sites in the test sample difficult. In performing IMS, a test sample image is desirably observed by a CCD camera or microscope during analysis; however, it is difficult to identify which site is being imaged when the crystal particles of the matrix cover the test sample. It is also difficult to confirm after analysis from which site a target material is obtained.

On the other hand, even when an inorganic matrix obtained by dispersing metal nanoparticles in a solution is used, similar to the case where an organic matrix is used, migration of a target material occurs because of the use of a dispersion medium, such as hexane or alcohol, making it difficult to accurately analyze the localization.

As a liquid matrix-free technique, IMS using gold vapor deposition has recently been suggested (NPL 5). This method has a feature in that gold is vapor deposited on the surface of a test sample to assist ionization. This method, however, has room for improvement because special equipment is required for the vapor deposition of gold nanoparticles, and the peaks of the target material are reduced or made undetectable due to the strong ion peaks originating from the gold appearing in the spectrum.

Accordingly, development of an improved method for imaging mass spectrometry using an ionization-assisting matrix of a test sample is desired, wherein the ionization efficiency is high, migration and visual information reduction are inhibited, no interference peaks originating from the matrix occur, and the analysis can be performed at high spatial resolution.

Additionally, PTL 5 and NPL 6 disclose other conventional techniques involving the present invention. These documents disclose a laser desorption ionization (LDI) plate having platinum particles as ionization-assisting particles that assist the ionization of a test sample. However, although these documents disclose that a dispersion in which platinum particles are dispersed is used to support the platinum particles on a plate, they do not suggest physical vapor depositing platinum on the surface of a test sample or applying it to imaging mass spectrometry.

CITATION LIST

Patent Literature

PTL 1: JP2008-232842A
PTL 2: JP2007-309860A
PTL 3: JP2007-157353A
PTL 4: JP2009-042206A
PTL 5: JP2008-204654A

Non-Patent Literature

NPL 1: Yasuhide NAITO, Mass Microprobe Aimed at Biological Samples, J. Mass Spectrom. Soc. Jpn., Vol. 53, No. 3, 2005, pp. 125-132
NPL 2: Ales Svatos, Mass spectrometric imaging of small molecules, Trends in Biotechnology, Vol. 28, 2010, pp. 425-434
NPL 3: Yuki Sugiura & Mitsutoshi Setou, Imaging Mass Spectrometry for Visualization of Drug and Endogenous Metabolite Distribution: Toward In Situ Pharmacometabolomes, J Neuroimmune Pharmacol, Vol. 5, 2010, pp. 31-43
NPL 4: Yuki Sugiura, Shuichi Shimma, and Mitsutoshi Setou, Two-Step Matrix Application Technique To Improve Ionization Efficiency for Matrix-Assisted Laser Desorption/Ionization in Imaging Mass Spectrometry, Anal. Chem. Vol. 78, 2006, pp. 8227-8235
NPL 5: Ho-Wai Tang, Wei Lu, Chi-Ming Che, and Kwan-Ming Ng, Gold Nanoparticles and Imaging Mass Spectrometry: Double Imaging of Latent Fingerprints, Anal. Chem. Vol. 82, 2010, pp. 1589-1593
NPL 6: Tetsu YONEZAWA, Hideya KAWASAKI, Akira TARUI, Takehiro WATANABE, Ryuichi ARAKAWA, Toshihiro SHIMADA, and Eumitaka MAFUNE, Detailed Investigation on the Possibility of Nanoparticles of Various Metal Elements for Surface-Assisted Laser Desorption/Ionization Mass Spectrometry, ANALYTICAL SCIENCES, VOL. 25, 2009, pp. 339-346.

SUMMARY OF INVENTION

Technical Problem

An object of the present invention is to provide an improved method for imaging mass spectrometry using an ionization-assisting matrix of a test sample, wherein the ionization efficiency is high, migration and visual information reduction are inhibited, no interference peaks originating from the matrix occur, and the analysis can be performed at high spatial resolution.

Solution to Problem

The present inventors conducted extensive research to achieve the above object. As a result, they found that the above object can be achieved by preparing a sample by physical vapor depositing platinum nanoparticles on the surface of a test sample to be subjected to imaging mass spectrometry, and accomplished the present invention.

Specifically, the present invention relates to a method for imaging mass spectrometry and a method for preparing a sample for imaging mass spectrometry shown below.

Item 1

A method for imaging mass spectrometry using a sample prepared by physical vapor depositing platinum nanoparticles on a surface of a test sample to be subjected to imaging mass spectrometry.

Item 2

The method according to Item 1, wherein the platinum nanoparticles have an average particle size of 2 to 20 nm.

Item 3

The method according to Item 1 or 2, wherein a platinum nanoparticle layer formed by the physical vapor deposition has a thickness of 2 to 50 nm.

Item 4

The method according to any one of Items 1 to 3, wherein the physical vapor deposition is based on magnetron sputtering.

Item 5

The method according to any one of Items 1 to 4 using a matrix assisted laser desorption/ionization (MALDI) imaging mass spectrometer.

Item 6

A method for preparing a sample for imaging mass spectrometry, comprising physical vapor depositing platinum nanoparticles on a surface of a test sample to be subjected to imaging mass spectrometry.

Item 7

The method according to item 6, wherein the platinum nanoparticles have an average particle size of 2 to 20 nm.

Item 8

The method according to Item 6 or 7, wherein a platinum nanoparticle layer formed by the physical vapor deposition has a thickness of 2 to 50 nm.

Item 9

The method according to any one of Items 6 to 8, wherein the physical vapor deposition is based on magnetron sputtering.

The method for imaging mass spectrometry and the method for preparing a sample for imaging mass spectrometry of the present invention are explained in detail below.

The method for imaging mass spectrometry of the present invention has a feature in that it uses a sample prepared by physical vapor depositing platinum nanoparticles on the surface of a test sample to be subjected to imaging mass spectrometry.

In the method for imaging mass spectrometry of the present invention having the above feature, platinum nanoparticles act as an ionization-assisting matrix for a test sample, thus attaining high ionization efficiency and spatial resolution. Further, since the migration of the test sample is inhibited because no liquid matrix is used, and physical vapor deposition of platinum nanoparticles does not result in reducing visual information on the surface of the test sample, the surface of the test sample can be observed by a CCD camera or a microscope during analysis. Furthermore, since interference peaks originating from platinum nanoparticles cannot be substantially observed, peaks originating from the test sample can be analyzed with high accuracy. Such excellent effects are obtained presumably because physical vapor deposition makes it possible to adhere platinum nanoparticles having a uniform particle size to the surface of the test sample. The method for imaging mass spectrometry of the present invention can be widely used in imaging mass spectrometry in the fields of biochemistry, medical science, genomic drug discovery, and materials and nanotechnology.

The test sample to which the imaging mass spectrometry method of the present invention is applied is not limited, and examples include biological tissues and cell-containing biological specimens; specifically, tissue sections originating from animals and plants, and cultured cells of animals, plants, or microorganisms that are adhered and cultivated on plates. Examples of the plants include trees, plants, flowers, fruits, leaves, roots, stems, etc. Examples of the animals include internal organs, brain, tissues, skin, hair, cells, etc. A tissue section can be produced by thinly slicing a biological tissue after performing, as necessary, flash freezing, followed by vacuum drying or without any treatment. A cultured cell can be prepared, for example, by using laser microdissection. Examples of the target materials (analysis subjects) contained in the biological specimens include biological materials such as proteins, peptides, nucleic acids, saccharides, and lipids; synthetic low-molecular compounds such as agricultural chemicals and drugs administered to a living body; synthetic polymers; exogenous metabolites generated by metabolizing these compounds in biological tissues; etc.

As the test sample, test samples in the field of materials and nanotechnology can be used. Examples of the test sample include nonferrous metals, ceramics, functional materials, battery materials, optical materials, carbon fibers, automobile materials, graphites, activated carbons, interlayer insulation films, organic semiconductor materials, high-molecular materials, low-molecular materials, organic EL materials, additives, dyes, inks, etc.

In the method for imaging mass spectrometry of the present invention, a sample prepared by physical vapor depositing platinum nanoparticles on the surface of the test sample is used. The physical vapor deposition (PVD) is not limited as long as it is a method comprising evaporating platinum in a vacuum vessel, and depositing the platinum as a thin film on the surface of the test sample on a substrate, and examples include vacuum deposition, molecular beam deposition (MBE), ion plating, ion beam deposition, conventional sputtering, magnetron sputtering, ion beam sputtering, ECR sputtering, etc. Of these physical vapor deposition methods, magnetron sputtering is preferred in the present invention.

Magnetron sputtering is conventionally used for imparting conductivity to the surface of an insulator sample as a pretreatment for high-resolution scanning electron microscope (HR-SEM) observation. For example, the method disclosed in the previous report (I. STOKROOS, D. KALICHARAN, J. J. L. VAN DER WANT, W. L. JONGEBLOED, Journal of Microscopy, Vol. 189, 1998, pp. 79-79) can be used as magnetron sputtering used in the present invention.

Platinum nanoparticles deposited on the surface of the test sample by physical vapor deposition preferably have an average particle size of 2 to 20 nm, and more preferably 2 to 10 nm. The particle size distribution is preferably 1 to 10, and more preferably 1 to 5. The deposition layer (platinum nanoparticle layer) preferably has a thickness of 2 to 50 nm, and more preferably 10 to 30 nm. The platinum nanoparticles deposited by physical vapor deposition, which are different from commercially available platinum nanoparticles, are pure platinum nanoparticles in which a protective agent (organic molecules, polymer, etc.) is not adhered to the particle surface. The average particle size and particle size distribution of the platinum nanoparticles, and the thickness of the deposition layer in the present specification are values measured by electron microscope observation.

In the present invention, platinum nanoparticles having a uniform particle size can be deposited on the surface of the test sample by physical vapor deposition. The deposition of nano-order fine particles within the above range has no risk of reducing visual information on the surface of the test sample. Further, unlike the case of using a liquid matrix, the migration of the test sample can be inhibited. The platinum nanoparticles act as an ionization-assisting matrix for the test sample; however, since the platinum nanoparticles per se are not ionized by laser irradiation, and can efficiently assist the ionization of the test sample, high ionization efficiency and spatial resolution can be obtained, and the generation of interference peaks originating from the matrix can be avoided. Thus, in the present invention, the S/N ratio or sensitivity of a detection signal are improved, and peaks originating from the test sample can be analyzed with high accuracy.

FIG. 1 (a) is an SEM image obtained when platinum is vapor deposited on a carbon surface by a physical vapor deposition method, (b) is an SEM image obtained when gold is vapor deposited on the surface of an electromagnetic tape by a physical vapor deposition method, and (c) is an SEM image obtained when a conventional organic matrix (the organic matrix being sinapic acid) for MALDI is adhered by a spray method. A comparison of these SEM images reveals that nanoparticles having a highly uniform particle size can be homogeneously deposited by platinum physical vapor deposition. In contrast, the comparison also reveals that the particle size is increased and widely varies in gold physical vapor deposition compared to platinum physical vapor deposition. As is clear from the results of Example 5 and Comparative Example 1 described later, a platinum-vapor-deposited matrix ensures high accuracy imaging mass spectrometry compared to a gold-vapor-deposited matrix; such a difference in the results is presumably based on a difference in the uniformity of fine particles obtained by physical vapor deposition. Moreover, since interference peaks originating from gold particles are observed in gold vapor deposition, the platinum vapor deposition of the present invention has an advantage in this regard.

In the present invention, imaging mass spectrometry is performed using the sample prepared by the above technique. The present invention includes not only a method for imaging mass spectrometry but also a method for preparing a sample for imaging mass spectrometry using the above technique.

To perform imaging mass spectrometry using the above sample, the sample is irradiated with a laser to ionize the test sample. The wavelength of the laser is preferably about 250 to 600 nm, and is preferably adjusted by a condensing optical system so that the irradiation diameter on the test sample is 50 μm or less. Specifically, when the test sample, which is an analysis subject, is a cell, narrowing the laser beam irradiation diameter down to 10 μm or less (about several μm) is desired. In the present invention, when the platinum nanoparticles are irradiated with a small diameter laser beam, platinum nanoparticles absorb the laser beam to ionize the molecules of the test sample by the interaction (energy transition) of the platinum nanoparticles and the test sample, while the platinum nanoparticles are not ionized. Accordingly, in the method for imaging mass spectrometry of the present invention, there is no need to select a known matrix depending on the analysis subject, and the mass spectrometry can be performed by a uniform method; thus, operation is simpler than before.

After the ionization of the test sample, ionized molecules are detected. In the present invention, ionization, detection, and imaging can be carried out using the same imaging mass spectrometer (for example, the MALDI imaging mass spectrometer: "AutoFlex III": produced by Bruker Corporation); however, the device is not limited thereto, and commercially available MALDI can be used in combination with a commercially available imaging device.

In the present invention, imaging (two dimensions) mass spectrometry of the target material can be conducted by performing mass spectrometry and analysis at an arbitrary position of the sample. Since the present invention is a technique for physical vapor depositing platinum nanoparticles on the surface of a test sample, migration of the test sample and loss of visual information are avoided. Therefore, the surface of the test sample can be observed using a CCD camera or a microscope during analysis. As the CCD camera and microscope used in observation, a known CCD camera and microscope can be used according to an ordinary method.

Advantageous Effects of Invention

According to the method for imaging mass spectrometry of the present invention, platinum nanoparticles act as an ionization-assisting matrix for a test sample, thus ensuring high ionization efficiency and spatial resolution. Further, since the migration of the test sample is inhibited because no liquid matrix is used, and physical vapor deposition of platinum nanoparticles does not result in reducing visual information on the surface of the test sample, the surface of the test sample can be observed by a CCD camera or a microscope during analysis. Furthermore, since interference peaks originating from platinum nanoparticles cannot be substantially observed, peaks originating from the test sample can be analyzed with high accuracy. Such excellent effects are obtained presumably because physical vapor deposition makes it possible to adhere platinum nanoparticles having a uniform particle size to the surface of the test sample. The method for imaging mass spectrometry of the present invention can be widely used in imaging mass spectrometry in the fields of biochemistry, medical science, genomic drug discovery, and materials and nanotechnology.

(*b*) shows an SEM image obtained when gold is physical vapor deposited on a magnetic tape surface.

(*c*) shows an SEM image obtained when a conventional organic matrix for MALDI (the organic matrix being sinapic acid) is adhered by a spray method.

Figure 1:
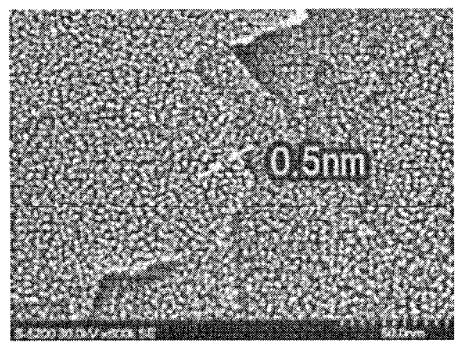
FIG. 1 (*a*) shows an SEM image obtained when platinum is physical vapor deposited on a carbon surface.
Figure 1:
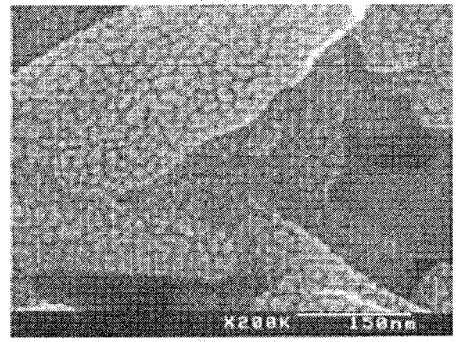
Figure 1:
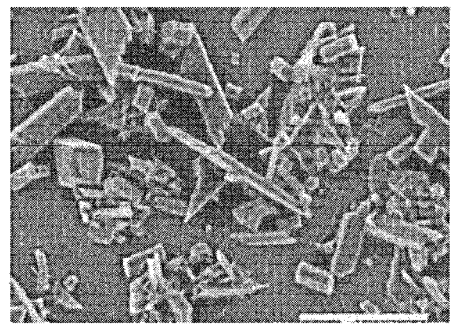
Figure 2:
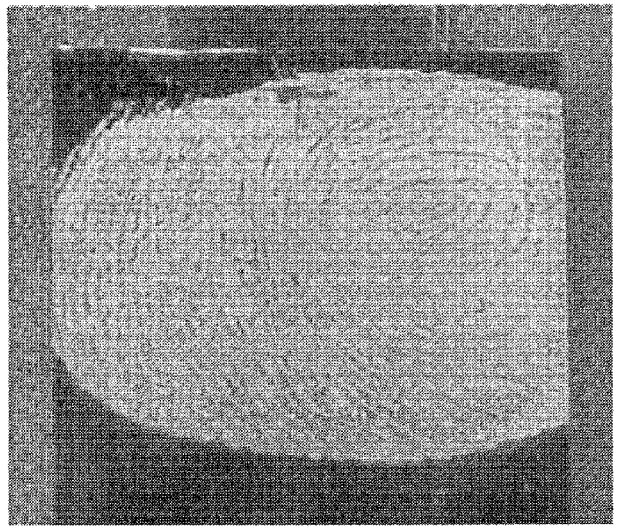

FIG. 2 shows that in Example 1, when platinum nanoparticles are physical vapor deposited after a finger is pressed on a slide glass, a fingerprint clearly emerges.

Figure 3:
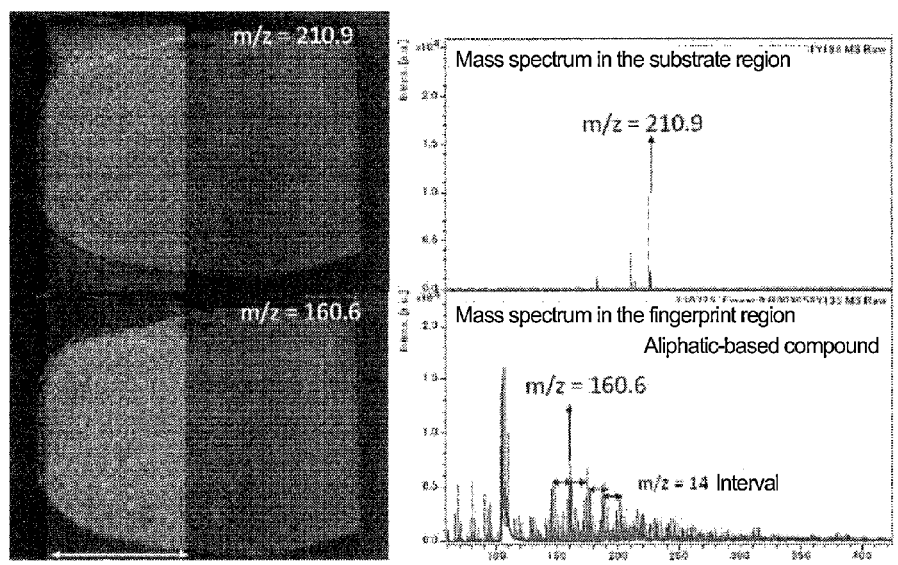

FIG. 3 shows a comparison between the mass spectrum (m/z) of the substrate region and the mass spectrum (m/z) of the fingerprint region in Example 1.

Figure 4:
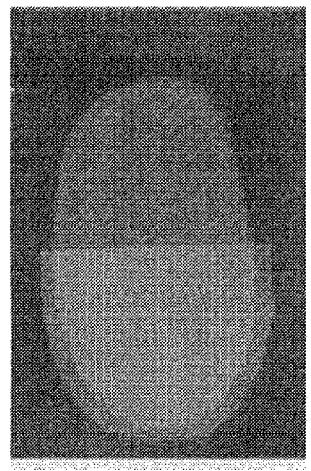
Figure 4:
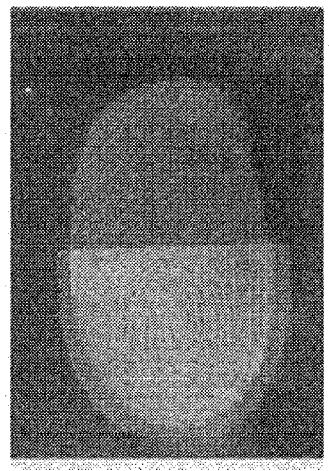
Figure 4:
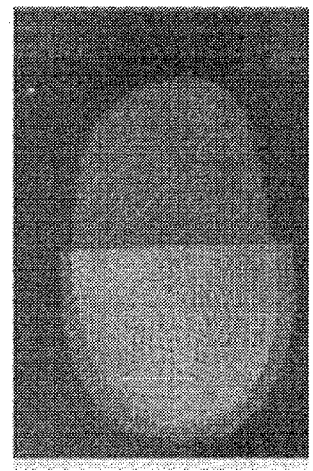

FIG. 4 shows the images of materials at a mass-to-charge ratio (m/z) of 1,000 or more present in the fingerprint region in Example 1.

Figure 5:
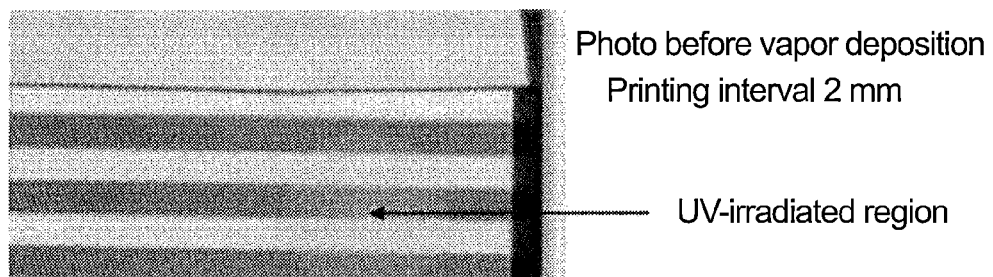
Figure 5:
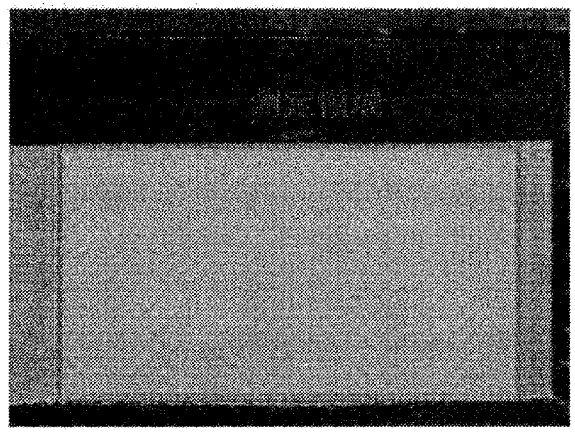

FIG. 5 (*a*) shows a stripe color-printing (magenta) region, and a region (white outlined against a colored background) in which the print is degraded by UV irradiation in Example 2.

(*b*) shows the state (sample) after the physical vapor deposition of platinum nanoparticles.

Figure 6:
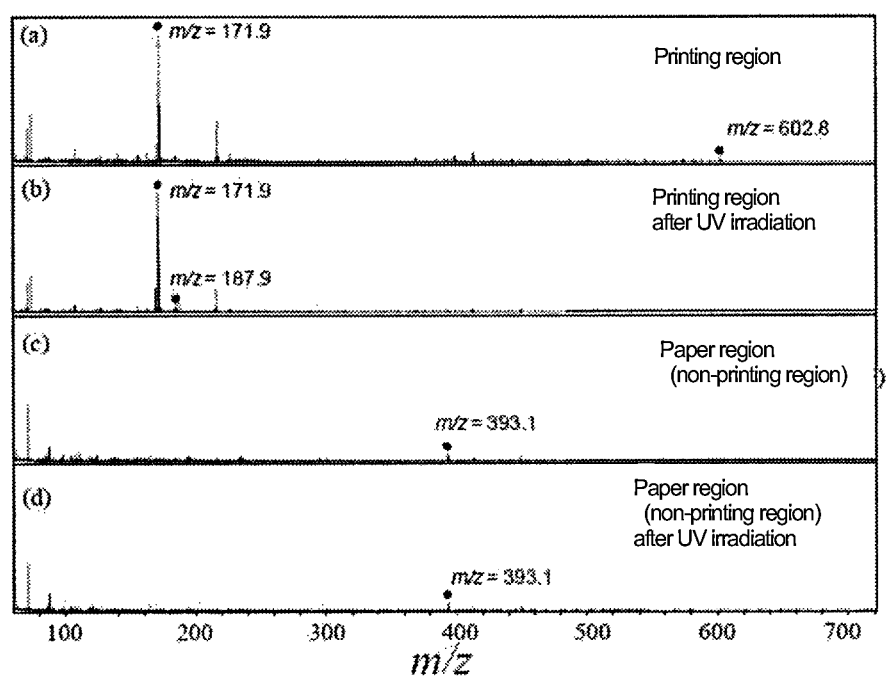

FIG. 6 shows the mass spectra (m/z) of the regions including the printing region, printing region after UV irradiation, paper region, and paper region after UV irradiation in Example 2.

Figure 7:
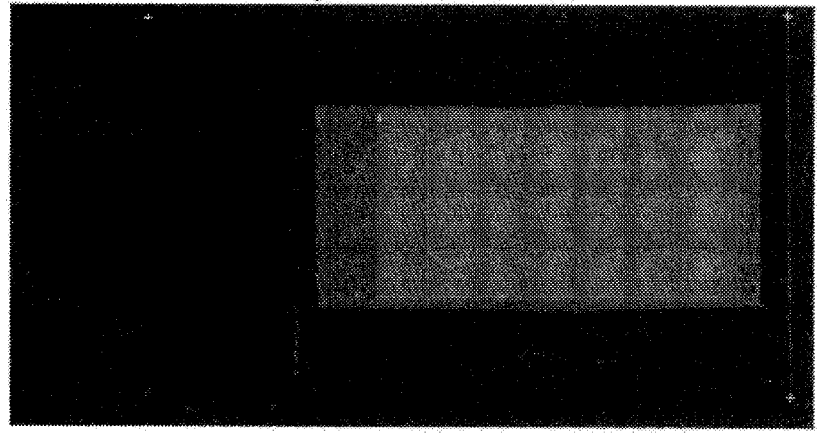
Figure 7:

FIG. 7 shows an image of material lost by UV irradiation in Example 2.

Figure 8:
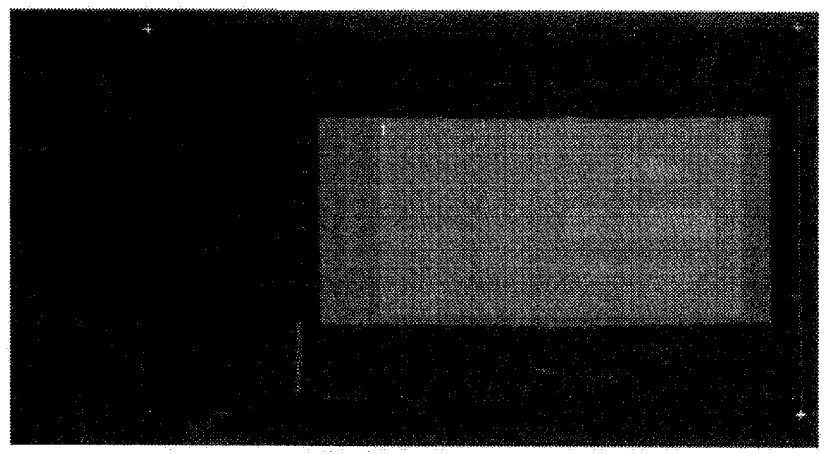

FIG. 8 shows an image of material decomposed by UV irradiation in Example 2.

Figure 9:
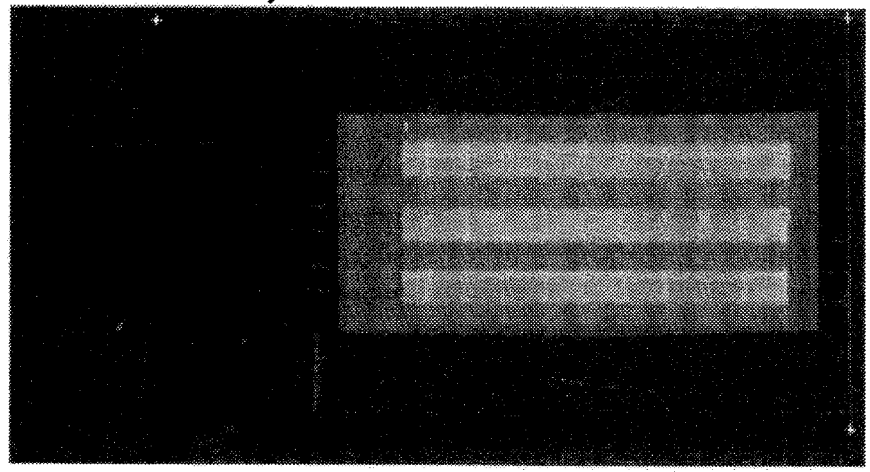

FIG. 9 shows an image of material that is not lost by UV irradiation in Example 2.

Figure 10:
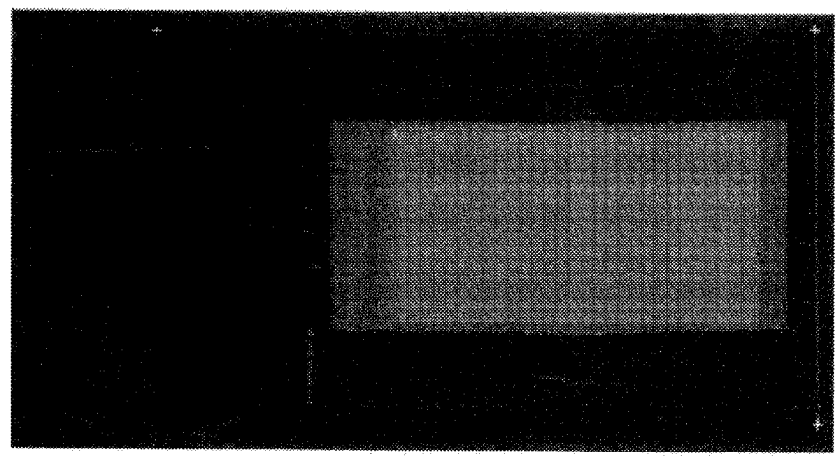

FIG. 10 shows an image of material distributed on the paper region in Example 2.

Figure 11:
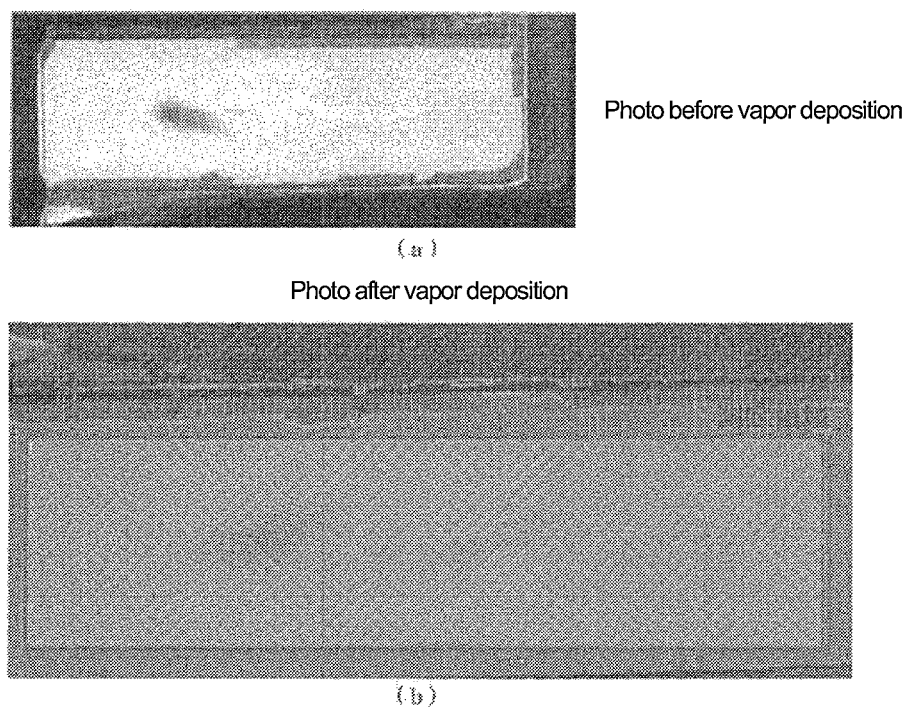

FIG. 11 (*a*) shows the state where three dyes are developed on TLC in Example 3.

(*b*) shows the state (sample) after the physical vapor deposition of platinum nanoparticles.

Figure 12:
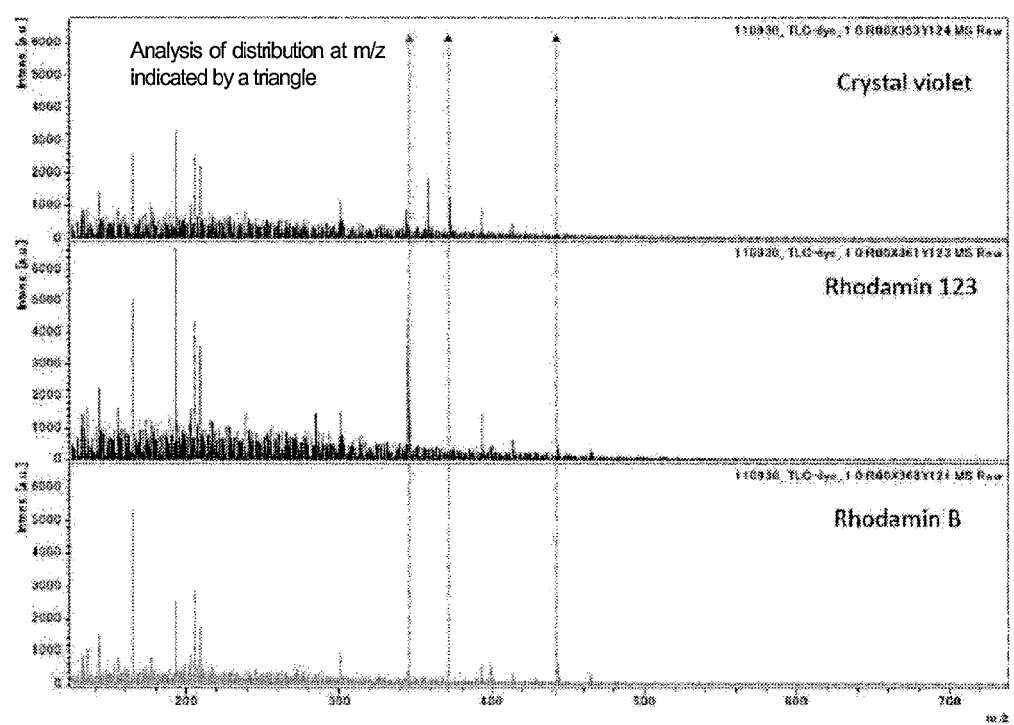

FIG. 12 shows the mass spectra (m/z) indicating that all of the three dyes are detected by mass spectrometry in Example 3.

Figure 13:
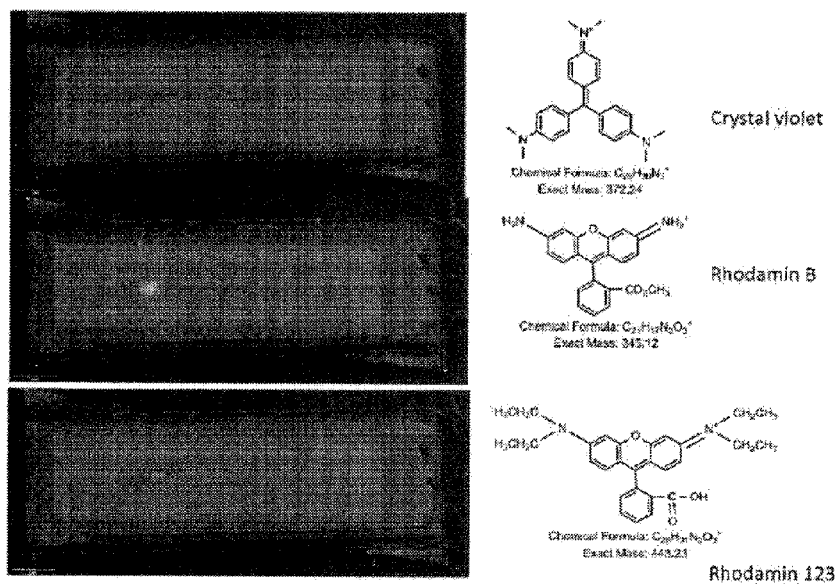

FIG. 13 shows images of the three dyes analyzed in Example 3.

Figure 14:
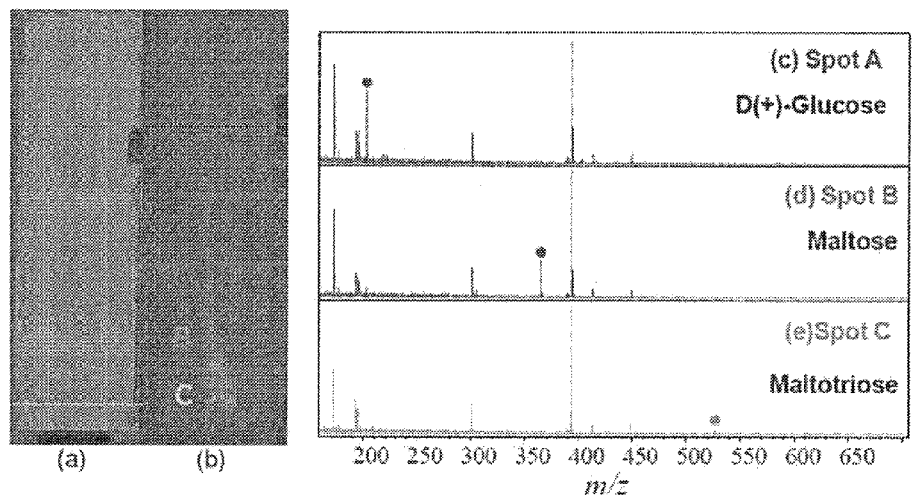

FIG. 14 (*a*) shows the state where three saccharides are developed on TLC in Example 4.

(*b*) shows an image of three saccharides analyzed.

(*c*), (*d*), and (*e*) show the mass spectra indicating the results of all of the three saccharides detected by mass spectrometry.

Figure 15:
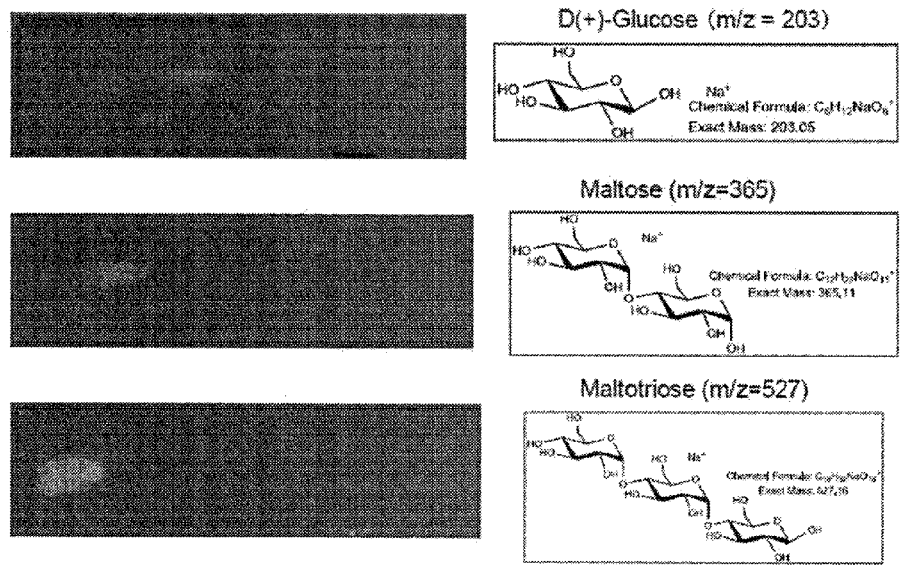

FIG. 15 shows the chemical structures of the three saccharides analyzed, and images of the three saccharides developed on TLC in Example 4.

Figure 16:
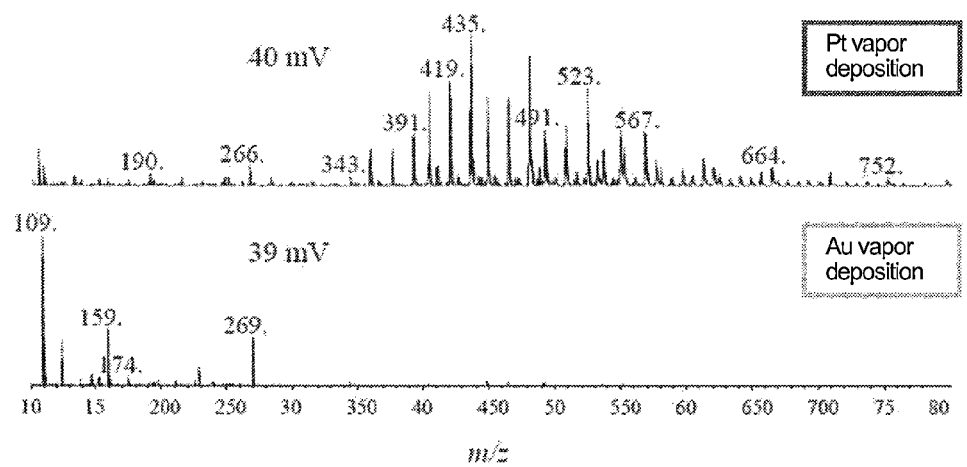

FIG. 16 relatively shows a difference of ion peaks originating from "#" signs written in black ink on the substrates in Example 5 (platinum vapor deposition) and Comparative Example 1 (gold vapor deposition).

Figure 17:
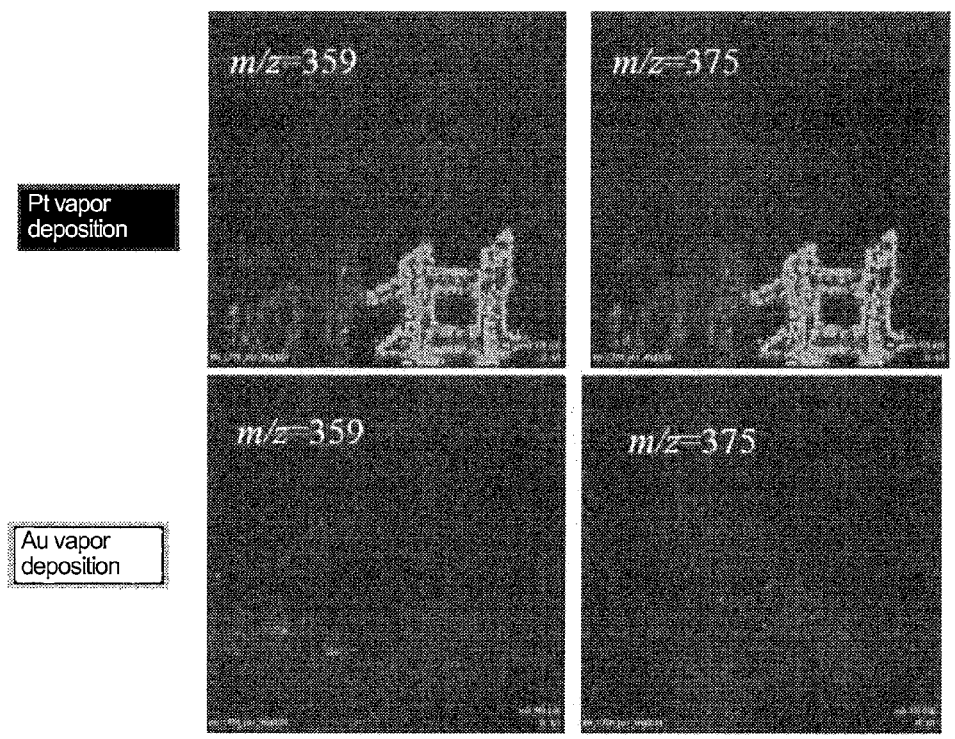

FIG. 17 shows that the imaging mass spectrometry capability is higher in platinum vapor deposition than in gold vapor deposition in Example 5 (platinum vapor deposition) and Comparative Example 1 (gold vapor deposition).

Figure 18:
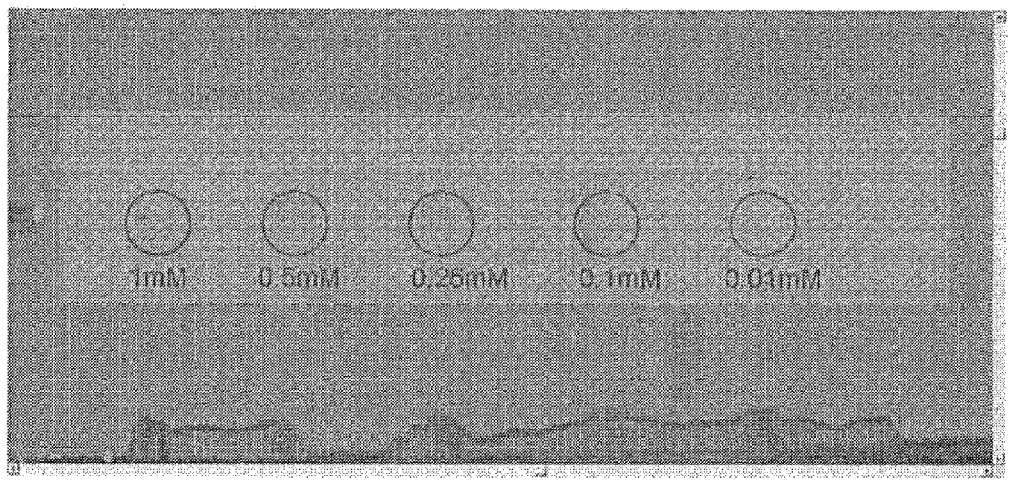

FIG. 18 shows the state where methylene blue solutions having different concentrations are added dropwise on TLC, and platinum nanoparticles are physical vapor deposited thereon in Example 6.

Figure 19:
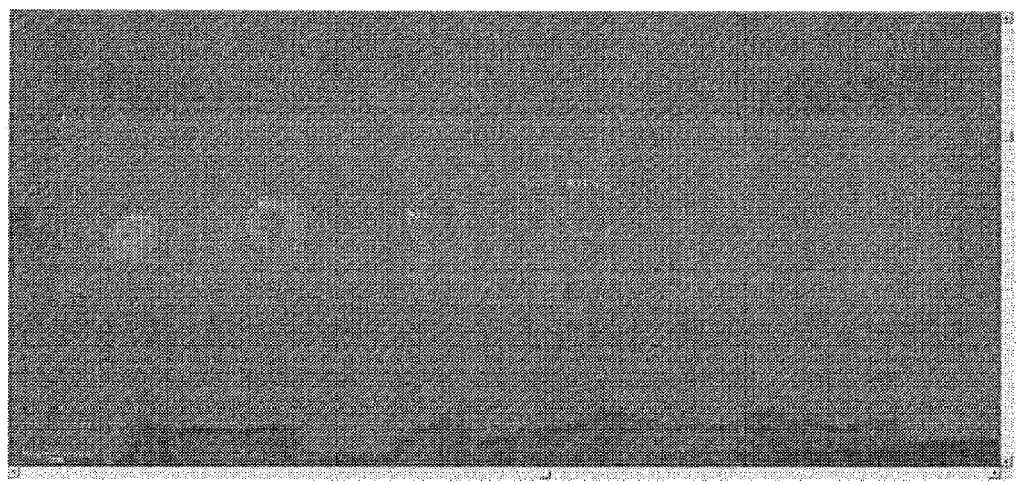

FIG. 19 shows an image obtained by imaging the ion peak distribution of a material at a mass-to-charge ratio (m/z) of 372 in Example 6.

Figure 20:
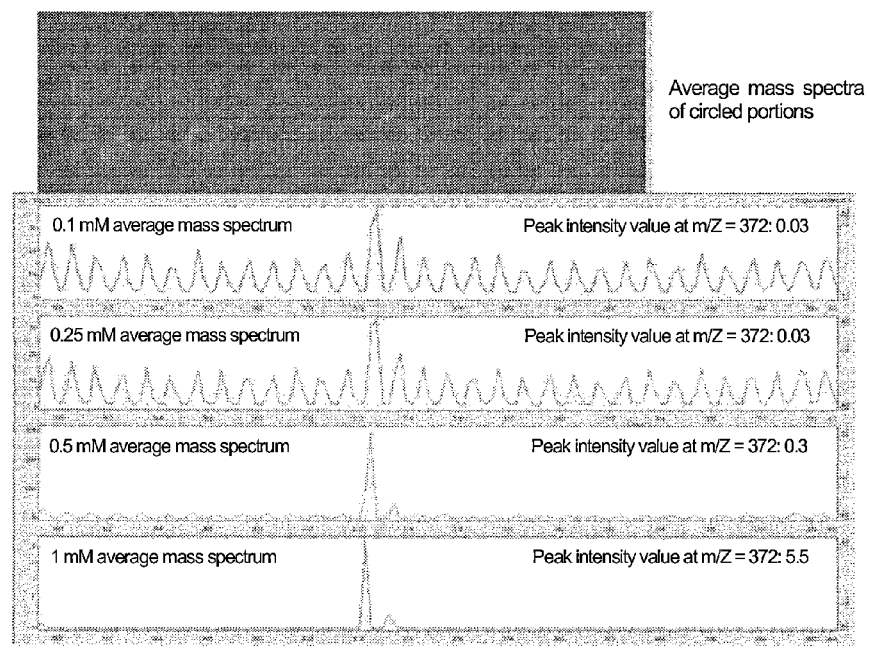

FIG. 20 shows the peak intensities of a material at a mass-to-charge ratio (m/z) of 372 detected at each concentration in Example 6.

Figure 21:
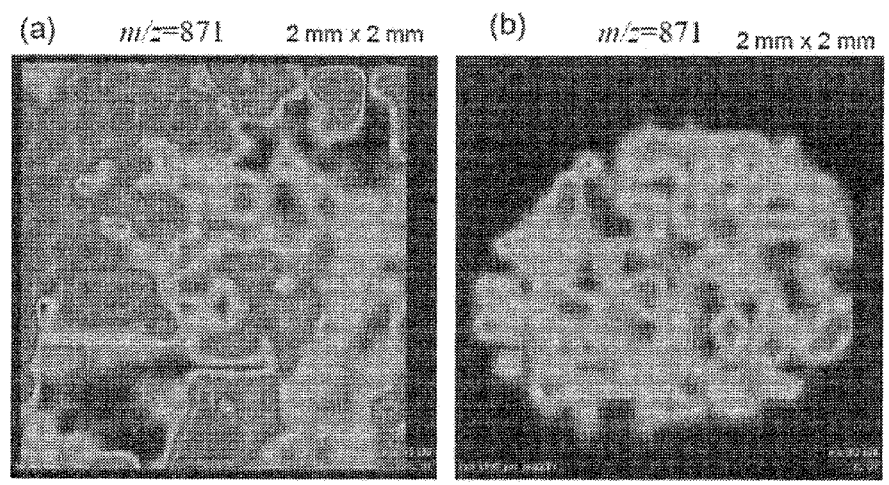

FIG. 21 (*a*) shows an IMS image of a sample obtained by applying a methanol dispersion of platinum nanoparticles (average particle size: 5 nm) on an ink spot in Example 7.

(*b*) shows an IMS image of a sample obtained by vapor depositing platinum on the ink spot.

Figure 22:
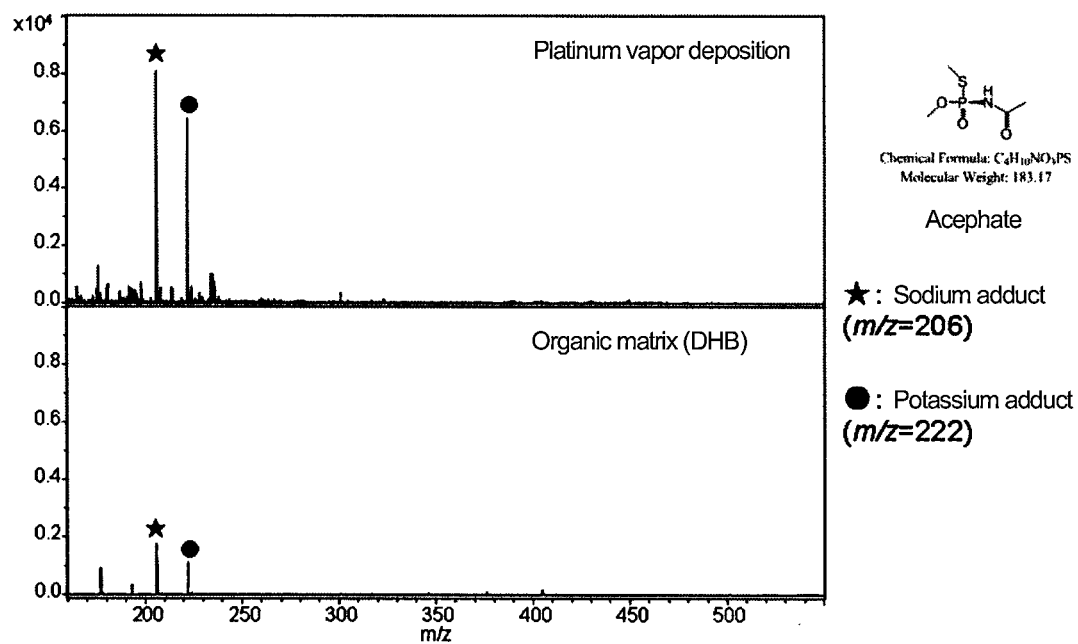

FIG. 22 shows the mass spectra obtained in Example 8 and Comparative Example 2.

Figure 23:
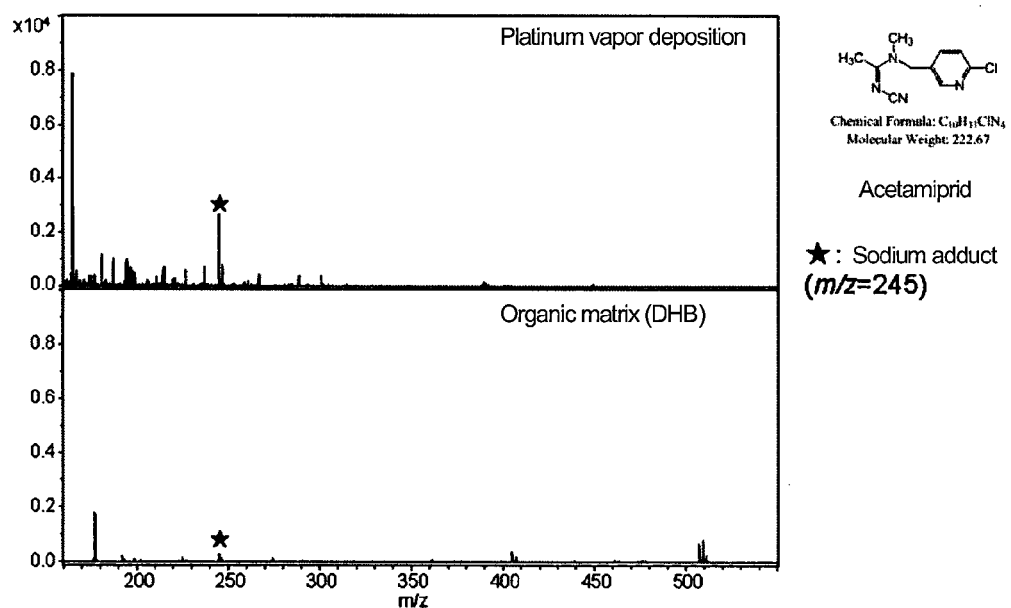

FIG. 23 shows the mass spectra obtained in Example 9 and Comparative Example 3.

Figure 24:
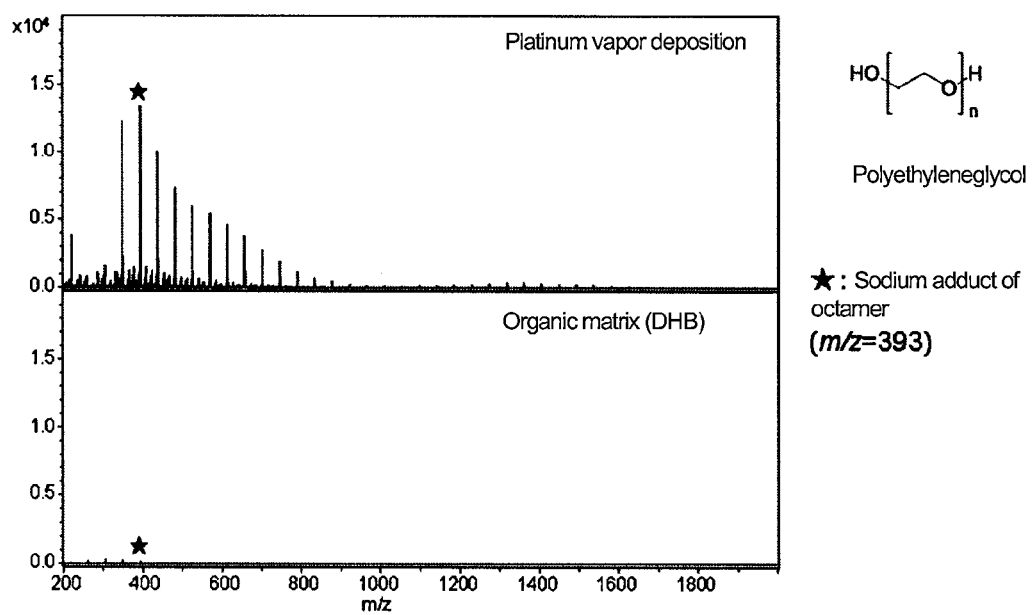

FIG. 24 shows the mass spectra obtained in Example 10 and Comparative Example 4.

Figure 25:
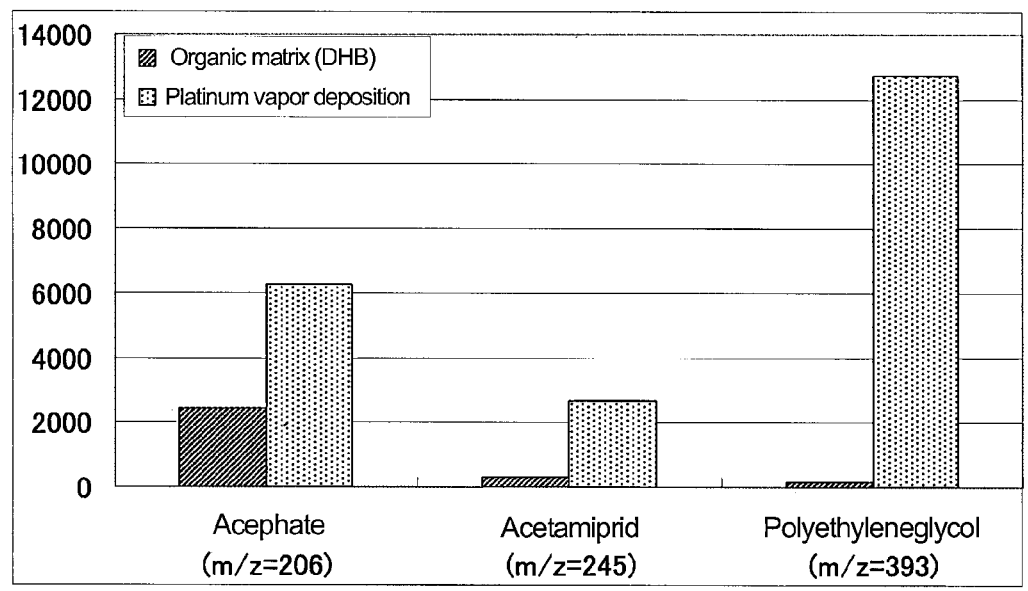

FIG. 25 shows a graph comparing the mass spectrum intensities obtained in Examples 8 to 10 and Comparative Examples 2 to 4.

Figure 26:
Figure 26:
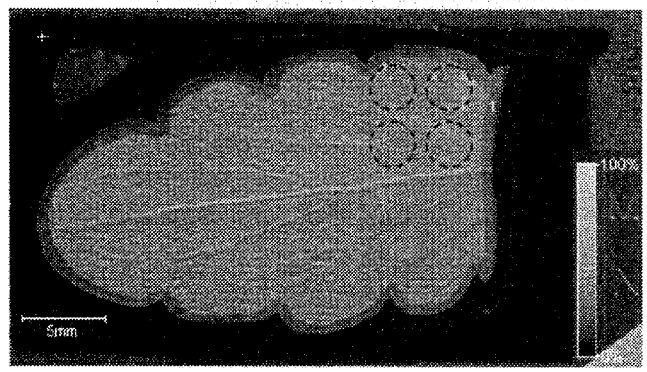
Figure 26:
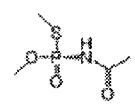

FIG. 26 visualizes the distribution of acephate in Example 8 and Comparative Example 2. The peak originating from acephate at m/z=206 was used. The dotted line circles outline drop areas.

Figure 27:
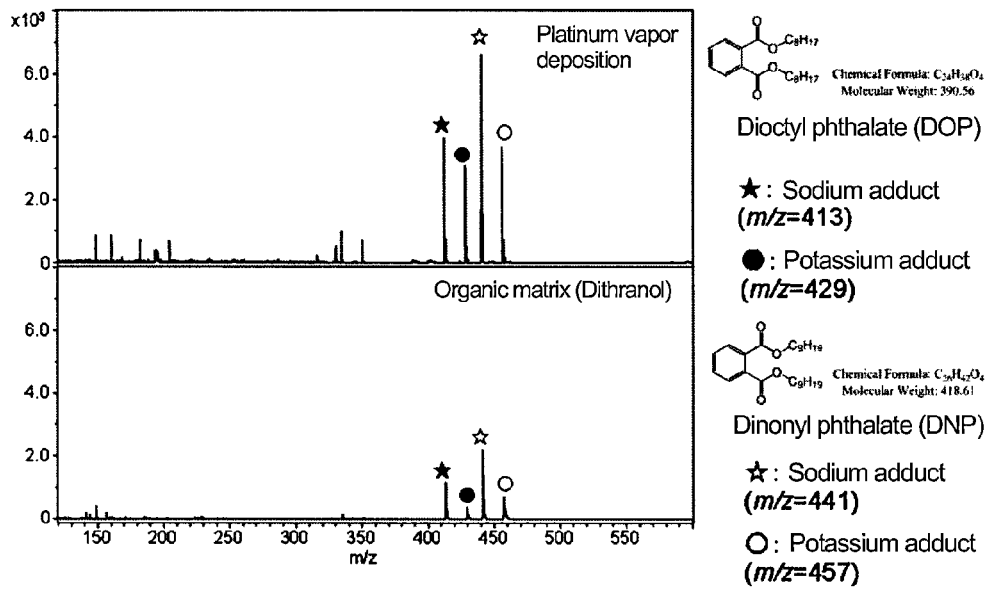

FIG. 27 shows the mass spectra obtained in Example 11 and Comparative Example 5.

Figure 28:
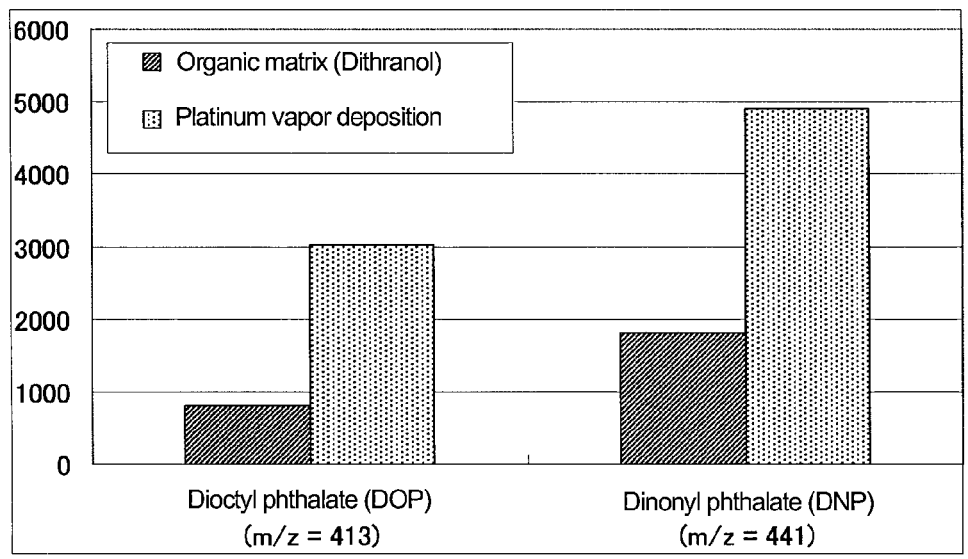

FIG. 28 shows a graph comparing the mass spectrum intensities obtained in Example 11 and Comparative Example 5.

Figure 29:
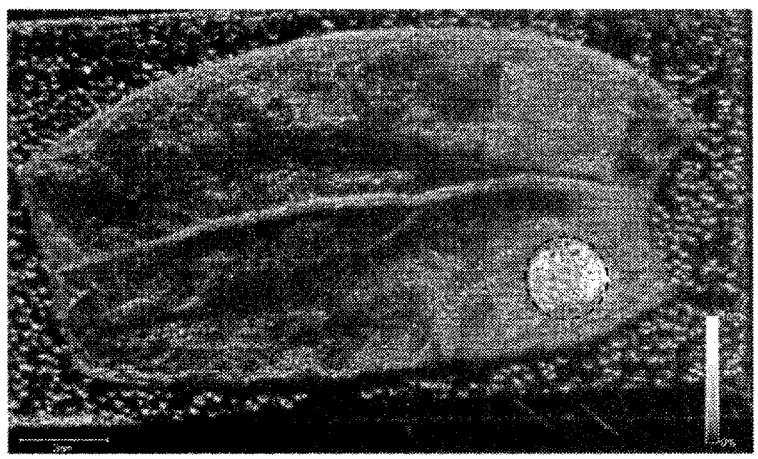

FIG. 29 visualizes the distribution of acetamiprid in Example 12. The peak originating from acetamiprid at m/z=245 was used. The dotted line circle outlines a drop area.

Figure 30:
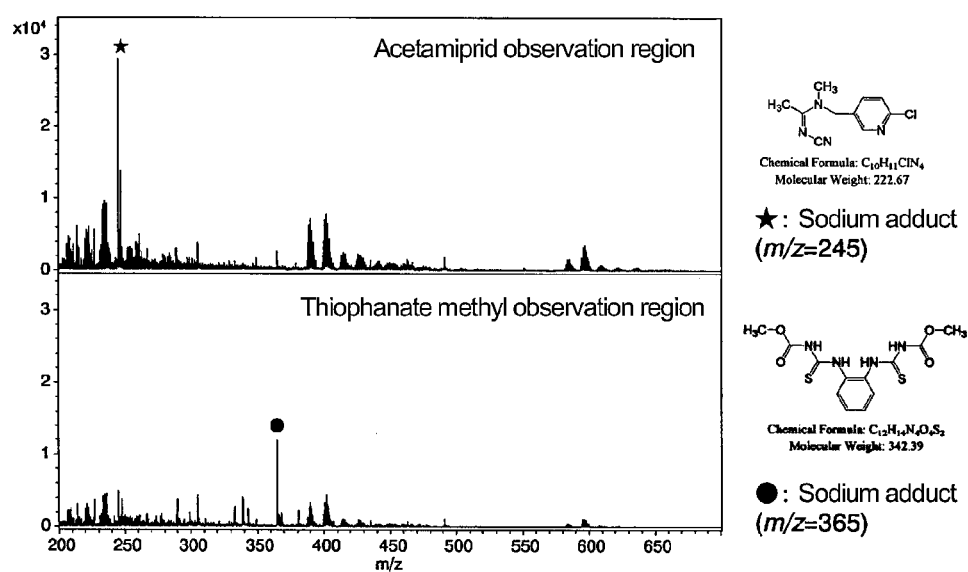

FIG. 30 shows the mass spectra obtained in Example 13.

Figure 31:
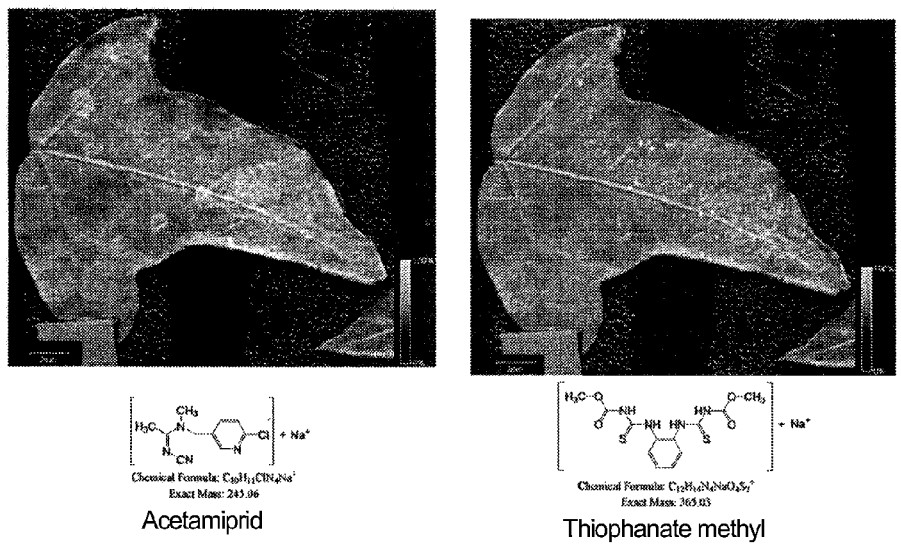

FIG. 31 visualizes two types of distributions, i.e., distributions of acetamiprid and thiophanate methyl in Example 13. The peak originating from acetamiprid at m/z=245, and the peak originating from thiophanate methyl at m/z=365 were used.

Figure 32:
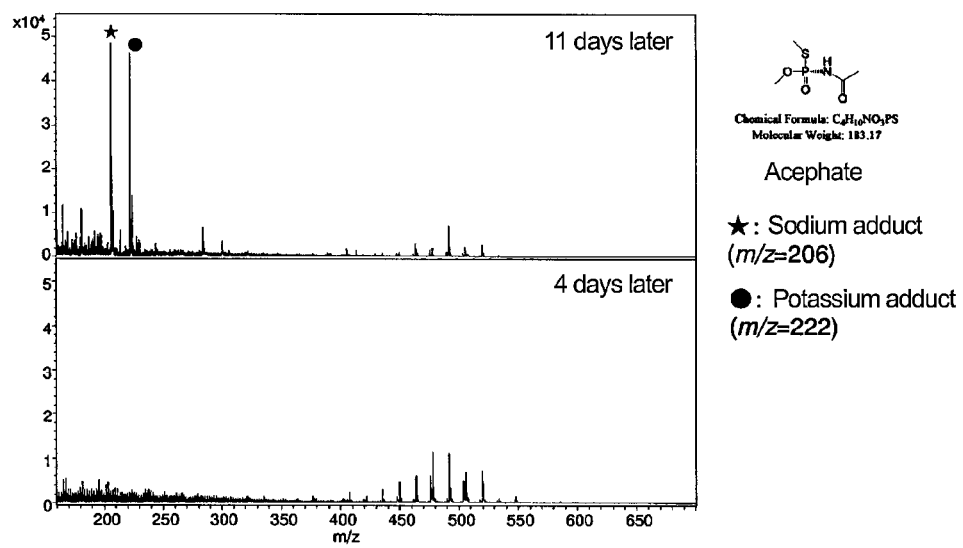

FIG. 32 shows the mass spectra obtained in Example 14.

Figure 33:
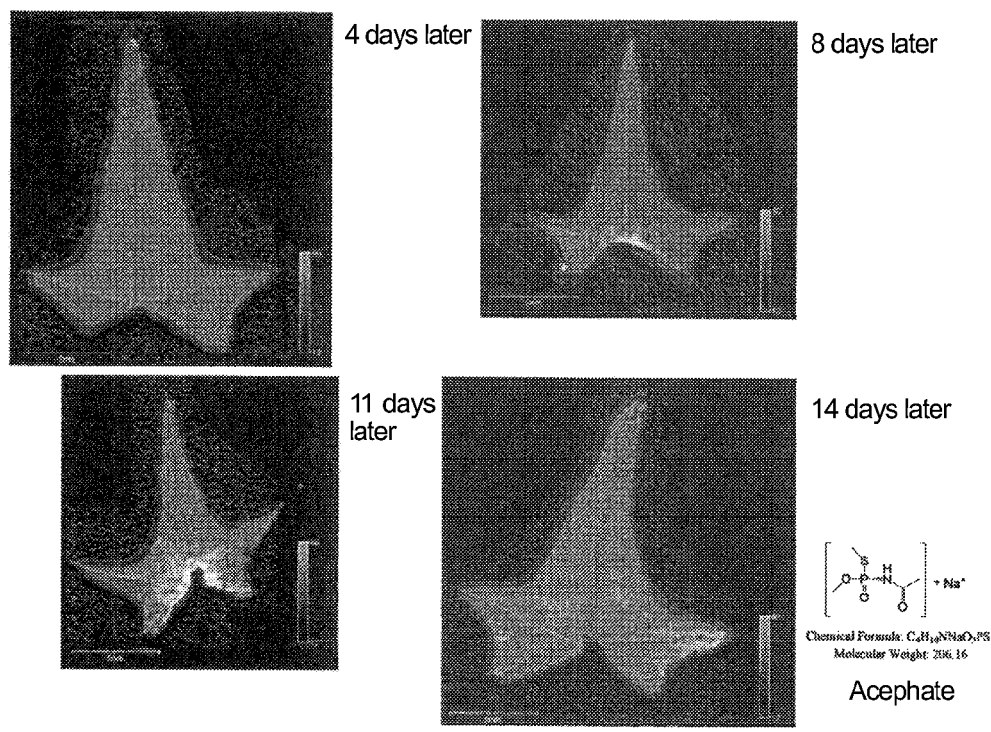

FIG. 33 visualizes the distribution of acephate on a leaf in Example 14. The peak originating from acephate at m/z=206 was used.

Figure 34:
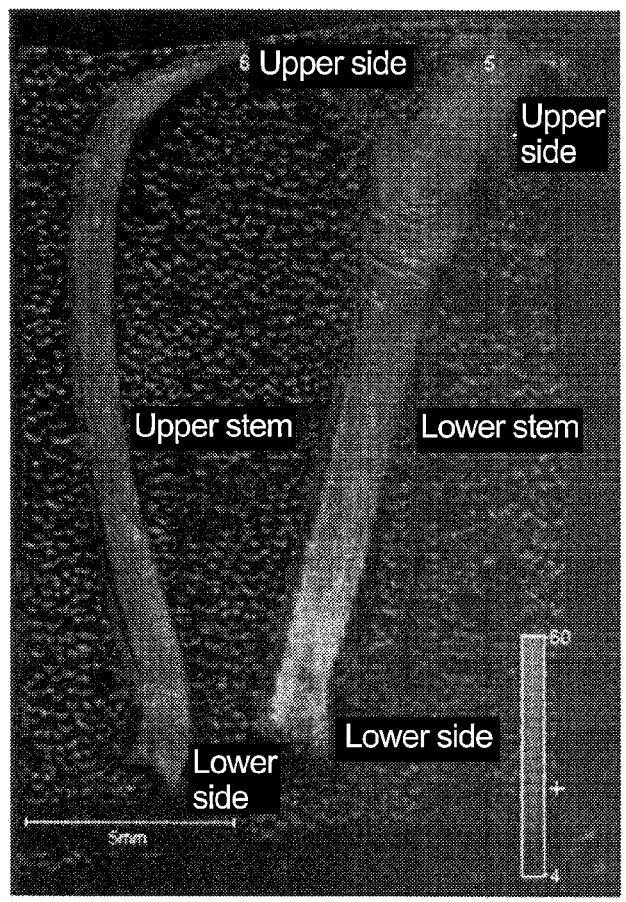
Figure 34:
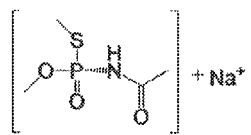

FIG. 34 visualizes the distribution of acephate of a stem in Example 14. The peak originating from acephate at m/z=206 was used.

DESCRIPTION OF EMBODIMENTS

The present invention is detailed below with reference to the Examples and Comparative Examples; however, the present invention is not limited thereto.

Example 1

Direct Analysis of Material Adhering to Finger by IMS

A finger was pressed on a chromium-coated slide glass. Platinum nanoparticles having an average particle size of 3 nm were thinly vapor deposited thereon using a magnetron sputtering device (device name: "E-1030" produced by Hitachi Ltd.) to a thickness of 20 nm. Consequentially, the fingerprint clearly emerged (see FIG. 2).

The fingerprint was measured and analyzed by IMS using a MALDI imaging mass spectrometer (device name: "AutoFlex III" produced by Bruker Corporation).

The measurement conditions of IMS are shown below.
Irradiation laser: Nd:YAG laser (355 nm)
Accelerating voltage: 19 kV
Reflectron voltage: 21 kV
Laser radius: about 100 μm (ultra mode)
Laser intensity: 60%
Measurement interval: 100 μm As a result, from the glass on which platinum was vapor deposited, many strong signals originating from the fingerprint were obtained between mass-to-charge ratios (m/z)=100 to 300 (see FIG. 3). In contrast, no peak originating from the fingerprint was observed from the glass on which platinum was not vapor deposited.

Since the measured peaks emerged at intervals of 14 Da ($CH_2$=14), the peaks were reasonably determined to be aliphatic-based compounds in the fingerprint. Of the obtained peaks, IMS analysis was performed particularly focusing on the peak at mass-to-charge ratio (m/z)=160.6. The results of the analysis corresponded to the distribution of the fingerprint region. In contrast, the peak originating from the glass substrate at mass-to-charge ratio (m/z)=210.9 was not detected in the fingerprint region. Further, peaks for three high-molecular-weight materials originating from the fingerprint were observed at a mass-to-charge ratio (m/z) of 1,000 or more (m/z=1,111, 1,135, and 1,187) in the fingerprint region, and the results of IMS analysis corresponded to the distribution of the fingerprint region (see FIG. 4).

The platinum vapor deposition allowed highly accurate mass spectrometry of the fingerprint region pressed on the glass. This technique is expected to be useful in scientific investigations, such as criminal investigations.

Example 2

Direct Analysis and Deterioration Evaluation of Print Paper by IMS

Using ink-jet printing, stripe color printing (magenta) was performed on paper at intervals of 2 mm. Subsequently, to evaluate degradation of the printed paper, a certain printed portion was irradiated with UV light for 30 minutes. The printed paper was degraded due to the UV irradiation, and discoloration (white outlined against a colored background) was observed (see FIG. 5 (a)).

Platinum nanoparticles having an average particle size of 3 nm were thinly vapor deposited thereon using a magnetron sputtering device (device name: "E-1030" produced by Hitachi Ltd.) to a thickness of 20 nm (see FIG. 5 (b)).

The sample was measured and analyzed by IMS using a MALDI imaging mass spectrometer (device name: "AutoFlex III" produced by Bruker Corporation). A sample on which platinum nanoparticles were not vapor deposited was prepared as a control sample.

The IMS measurement conditions are shown below.
Irradiation laser: Nd:YAG laser (355 nm)
Accelerating voltage: 19 kV
Reflectron voltage: 21 kV
Laser radius: about 100 μm (ultra mode)
Laser intensity: 70%
Measurement interval: 200 μm As a result, the peak for a magenta pigment component at m/z=602.8 was observed from the non-UV irradiated region (printed region) (see FIG. 6), and the distribution corresponded to the stripe printing pattern (see FIG. 7).

In contrast, no peak for a magenta pigment component at m/z=602.8 was observed from the UV-irradiated discolored region (printed region after UV irradiation) (see FIG. 6). Instead, from the UV-irradiated region (printed region after UV irradiation), a peak originating from a product decomposed by the UV irradiation newly appeared at m/z=187.9 (see FIG. 6), and the distribution corresponded to the UV-irradiated circle pattern (see FIG. 8).

Additionally, it was revealed that there was a pigment component at m/z=171.9 (see FIG. 9), which was not decomposed by the UV irradiation, and a component at m/z=393.1 (see FIG. 10), which was distributed in the paper region, and not decomposed by the UV irradiation.

Components of the pigment and paper could not be detected from the sample on which platinum nanoparticles were not vapor deposited. The platinum nanoparticle vapor deposition allowed the analysis of distributions of magenta pigment components, paper components, and materials generated by light degradation. This technique is expected to be useful for analyzing the distribution or degradation of components of printed portion and coating compositions.

Example 3

Direct Analysis of TLC-Separated Analyte by IMS 1

The mixed solution of three dyes (rhodamin B: green, rhodamine 123: red, and crystal violet: violet) was spotted on a thin-layer chromatography (TLC) plate, and developed on the TLC. In a visual observation of the dye spots that moved on the TLC plate, two (rhodamine 123: red, and crystal violet: violet) of the three dyes were confirmed; however, the other dye (rhodamine B: green) could not be confirmed (see FIG. 11 (a)).

Platinum nanoparticles having an average particle size of 3 nm were thinly vapor deposited thereon using a magnetron sputtering device (device name: "E-1030" produced by Hitachi Ltd.) to a thickness of 20 nm (see FIG. 11 (b)). A sample on which platinum nanoparticles were not vapor deposited was prepared as a control sample.

Each sample was measured and analyzed by IMS using a MALDI imaging mass spectrometer (device name: "AutoFlex III" produced by Bruker Corporation).

The measurement conditions of IMS are shown below.
Irradiation laser: Nd:YAG laser (355 nm)
Accelerating voltage: 19 kV
Reflectron voltage: 21 kV
Laser radius: about 100 μm (ultra mode)
Laser intensity: 40'6
Measurement interval: 200 μm As a result, all of the three dyes, i.e., rhodamine B, rhodamine 123, and crystal violet, were detected from the dye spots on the TLC (see FIG. 12).

The imaging analysis by IMS confirmed that rhodamine B, which could not be visually observed, was present while partially overlapping another dye spot (see FIG. 13). This revealed that rhodamine B could not be visually confirmed.

From the TLC plate on which platinum nanoparticles were not vapor deposited, none of the dyes were detected. This revealed that the physical vapor deposition of platinum nanoparticles allowed not only identification of a test sample separated on the TLC, but also identification of a test sample that could not be visually confirmed due to the overlap of the spots of the test sample components.

Example 4

Direct Analysis of TLC-Separated Analyte by IMS 2

The mixed solution of three saccharides (glucose, maltose, and maltotriose) was spotted on a thin-layer chromatography (TLC) plate, and developed on the TLC. The saccharide spots moved on the TLC plate could not be visually observed (see FIG. 14 (a)). Platinum nanoparticles having an average particle size of 3 nm were thinly vapor deposited thereon using a magnetron sputtering device (device name: "E-1030" produced by Hitachi Ltd.) to a thickness of 20 nm. The sample was measured and analyzed by IMS using a MALDI imaging mass spectrometer (device name: "AutoFlex III" produced by Bruker Corporation).

The measurement conditions of INS are shown below.
Irradiation laser: Nd:YAG laser (355 nm)
Accelerating voltage: 19 kV
Reflectron voltage: 21 kV
Laser radius: about 100 μm (ultra mode)
Laser intensity: 50%
Measurement interval: 300 μm The imaging analysis by IMS confirmed three spots, A, B, and C, on the TLC (see FIG. 14 (b)). The mass spectrum of each spot revealed that spots A, B, and C were respectively glucose, maltose, and maltotriose (see FIGS. 14 (c), (d), and (e), and FIG. 15).

The imaging analysis by IMS confirmed the presence of saccharides that could not be visually observed. In general, since saccharides are colorless, the location of spots moved on TLC is confirmed by developing a color by oxidation or chemical modification of saccharides. The imaging analysis by IMS revealed that saccharides could be confirmed without this color developing operation.

From the TLC plate on which platinum nanoparticles were not physical vapor deposited, none of the saccharide components were detected. This revealed that the physical vapor deposition of platinum nanoparticles allowed not only identification of a test sample separated on a TLC, but also identification of a test sample that could not be visually confirmed due to the lack of color.

Example 5 and Comparative Example 1

Difference Between Platinum Vapor Deposition and Gold Vapor Deposition

A "#" sign was drawn in black ink used for injector printing on each substrate. Two samples, i.e., a sample in which platinum was physical vapor deposited on one substrate (Example 5) and a sample in which gold was physical vapor deposited on the other substrate (Comparative Example 1) were prepared. These substrates were subjected to imaging mass spectrometry. The imaging mass spectrometry was performed using a MALDI imaging mass spectrometer (device name; "AXIMA-CFR plus" made by Shimadzu Corporation.)

The measurement conditions of IMS are shown below.
Irradiation laser: Nitrogen laser (337 nm)
Accelerating voltage: 20 kV
Linear mode measurement (positive ion mode)
Laser radius: about 100 μm
Laser intensity: 60 (reading of the device)
Measurement interval: 100 μm Compared to gold vapor deposition, strong ion peaks originating from the black ink were observed on the substrate on which platinum was vapor deposited (see FIG. 16). The ion peak distributions at m/z=359 and 375 originating from the black ink components were imaged. In the substrate on which platinum was vapor deposited, the "#" sign emerged; however, in the substrate on which gold was vapor deposited, an image including the sign drawn in black ink was not obtained (see FIG. 17). This is presumably because platinum has higher detection sensitivity than gold.

Example 6

Concentration Dependency of Platinum Vapor Deposition

Methylene blue (five concentrations: 1 mM, 0.5 mM, 0.25 mM, 0.1 mM, and 0.01 mM) was separately added dropwise to a TLC plate, followed by platinum physical vapor deposition (see FIG. 18). Subsequently, imaging mass spectrometry was carried out. The imaging mass spectrometry was performed using a MALDI imaging mass spectrometer (device name: "AXIMA-CFR plus" produced by Shimadzu Corporation).

The measurement conditions of IMS are shown below.
Irradiation laser: nitrogen laser (337 nm)
Accelerating voltage: 20 kV
Linear mode measurement (positive ion mode)
Laser radius: about 100 μm
Laser intensity: 60 (reading of the device)
Measurement interval: 100 μm The ion peak distribution at m/z=372 was imaged. The peak intensity was reduced according to the concentration between 1 to 0.25 mM, locally detected at 0.1 mM, and not detected at 0.01 mM (see FIG. 19). FIG. 20 shows the peak intensity values at m/z=372 detected at each concentration.

The results indicated that in the sample of the present invention on which platinum was vapor deposited, the peak intensity and image dense were gradually shifted according to the concentration of the target material.

Example 7

Difference Between Platinum Vapor Deposition and Platinum Nanoparticle Dispersion A round ink spot was drawn in black ink on each paper. Two samples, i.e., a sample in which a methanol dispersion of platinum nanoparticles was applied to an ink spot, and a sample in which platinum was physical vapor deposited on the other ink spot, were prepared to conduct imaging mass spectrometry. The imaging mass spectrometry was performed using a MALDI imaging mass spectrometer (device name: "AXIMA-CFR plus" produced by Shimadzu Corporation).

The measurement conditions of IMS are shown below.
Irradiation laser: nitrogen laser (337 nm)
Accelerating voltage: 20 kV
Linear mode measurement (positive ion mode)
Laser radius: about 100 μm
Laser intensity: 60 (reading of a device)
Measurement interval: 100 μm Compared to the ink spot on which the methanol dispersion of platinum nanoparticles was applied, a round image originating from the black ink emerged in the ink spot on which platinum was vapor deposited (see FIG. 21 (b)). In the case where the platinum nanoparticle dispersion was used, since the black ink was dissolved in methanol, the ink spot configuration was not obtained (see FIG. 21 (a)). This is presumably because platinum vapor deposition exhibits higher detection sensitivity than the application of the platinum nanoparticle dispersion.

The results indicated that in the platinum-vapor-deposited sample of the present invention, the image could be obtained without changing the location of the test sample due to the solvent.

Examples 8 to 10 and Comparative Examples 2 to 4

Difference Between Platinum Vapor Deposition and Known Organic Matrix

Example 8

Acephate, Platinum Vapor Deposition

An aqueous solution of acephate (agricultural chemical) was added dropwise to a leaf of viola, followed by drying. Platinum nanoparticles were then vapor deposited using a magnetron sputtering device (E-3010: produced by Hitachi Ltd.) to a thickness of 10 nm, thereby preparing a sample.

Example 9

Acetamiprid, Platinum Vapor Deposition

An aqueous solution of acetamiprid (agricultural chemical) was added dropwise to a leaf of viola, followed by drying. Platinum nanoparticles were then vapor deposited using a magnetron sputtering device (E-3010: produced by Hitachi Ltd.) to a thickness of 10 nm, thereby preparing a sample.

Example 10

Polyethylene Glycol, Platinum Vapor Deposition

An aqueous solution of polyethylene glycol (synthetic polymer) was added dropwise to a leaf of viola, followed by drying. Platinum nanoparticles were then vapor deposited using a magnetron sputtering device (E-3010: produced by Hitachi Ltd.) to a thickness of 10 nm, thereby preparing a sample.

Comparative Example 2

Acephate, Known Organic Matrix

A sample was prepared in the same manner as in Example 8 except that the organic matrix layer of 2,5-dihydroxybenzoic acid (DHB) was formed using a matrix spraying device for MALDI imaging mass spectrometry (TM-sprayer: produced by HTX Imaging) in place of platinum vapor deposition.

Comparative Example 3

Acetamiprid, Known Organic Matrix

A sample was prepared in the same manner as in Example 9 except that the organic matrix layer of 2,5-dihydroxybenzoic acid (DHB) was formed using a matrix spraying device for MALDI imaging mass spectrometry (TM-sprayer: produced by HTX Imaging) in place of platinum vapor deposition.

Comparative Example 4

Polyethylene Glycol, Known Organic Matrix

A sample was prepared in the same manner as in Example 10 except that the organic matrix layer of 2,5-dihydroxybenzoic acid (DHB) was formed using a matrix spraying device for MALDI imaging mass spectrometry (TM-sprayer: produced by HTX Imaging) in place of platinum vapor deposition.

Each sample was measured and analyzed by IMS using a MALDI imaging mass spectrometer (device name: "AutoFlex III" produced by Bruker Corporation).

The measurement conditions of INS are shown below.
Irradiation laser: Nd:YAG laser (355 nm)
Accelerating voltage: 19 kV
Reflectron voltage: 21 kV
Laser radius: about 100 μm (ultra mode)
Laser intensity: 50%
Measurement interval: 300 μm Analysis Results FIG. 22 shows the results of Example 8 and Comparative Example 2. FIG. 23 shows the results of Example 9 and Comparative Example 3. FIG. 24 shows the results of Example 10 and Comparative Example 4.

The results of FIGS. 22 to 24 indicate that the peaks of target components were detected with high sensitivity in Examples 8 to 10 in which platinum vapor deposition was performed compared to Comparative Examples 2 to 4 in each of which an organic matrix layer was formed.

FIG. 25 shows the peak intensities of Examples 8 to 10 and Comparative Examples 2 to 4. It was confirmed that Examples 8 to 10 in which platinum vapor deposition was performed exhibited a sensitivity enhancing effect 3 to 100 times higher than that of Comparative Examples 2 to 4 in each of which an organic matrix layer was formed.

The results of the analysis of acephate distribution in Example 8 and Comparative Example 2 indicated that in Example 8, a strong peak of acephate was observed in the drop area, whereas the peak of acephate observed in Comparative Example 2 was weak (FIG. 26). Further, in Comparative Example 2, a peak of acephate was also observed from a non-drop area due to the migration effect of the solvent used for forming the organic matrix layer. Since the surface of a leaf has an uneven configuration and includes a wax layer, it is likely to repel a solvent and evoke a migration effect when compared to a slice test sample. However, in the platinum vapor deposition used in the Examples, peaks were confirmed only in the drop area, indicating that the migration effect was reduced.

Example 11 and Comparative Example 5

Difference Between Platinum Vapor Deposition and Known Organic Matrix

Example 11

DOP and DNP, Platinum Vapor Deposition

Platinum nanoparticles were vapor deposited on a polyvinyl chloride (PVC) wallpaper using a magnetron sputtering device (E-3010: made by Hitachi Ltd.) to a thickness of 10 nm. The PVC contained dioctyl phthalate (DOP) and dinonyl phthalate (DNP) as additives (plasticizers).

Comparative Example 5

DOP and DNP, Known Organic Matrix

A sample was prepared in the same manner as in Example 11 except that the organic matrix layer of 1,8-dihydroxy-9 (10H)-anthracenone (Dithranol) was formed using a matrix spraying device for MALDI imaging mass spectrometry (TM-sprayer: produced by HTX Imaging) in place of platinum vapor deposition.

Each sample was measured and analyzed by IMS using a MALDI imaging mass spectrometer (device name: "AutoFlex III" produced by Bruker Corporation).

The measurement conditions of IMS are shown below.
Irradiation laser: Nd:YAG laser (355 nm)
Accelerating voltage: 19 kV
Reflectron voltage: 21 kV
Laser radius: about 100 μm (ultra mode)
Laser intensity: 70%
Measurement interval: 300 μm
Analysis Results FIG. 27 shows the results of Example 11 and Comparative Example 5.

The results of FIG. 27 indicate that the peaks of target components (DOP and DNP) were observed with high sensitivity in Example 11 in which platinum vapor deposition was performed compared to Comparative Example 5 in which the organic matrix layer was formed.

FIG. 28 shows the peak intensities in Example 11 and Comparative Example 5. It was confirmed that Example 11 in which platinum vapor deposition was performed exhibited a sensitivity enhancing effect 3 to 4 times higher than that of Comparative Example 5 in which the organic matrix layer was formed.

The results of Examples 8 to 11 and Comparative Examples 2 to 5 indicate that the peaks of target components were observed with high sensitivity in the Examples in which platinum vapor deposition was performed compared to the cases where the known organic matrix layers (e.g., DHB and Dithranol) were formed.

Example 12

Acetamiprid, Platinum Vapor Deposition

In Example 9, the measurement conditions of IMS were changed as follows. Specifically, the laser diameter was reduced, and measurement was performed in high spatial resolution mode.

The measurement conditions of IMS are shown below.
Irradiation laser: Nd:YAG laser (355 nm)
Accelerating voltage: 19 kV
Reflectron voltage: 21 kV
Laser radius: about 50 μm (minimum mode)
Laser intensity: 50,
Measurement interval: 50 μm The results of the analysis of acetamiprid distribution obtained in high spatial resolution mode at measurement intervals of 50 μm confirmed that acetamiprid was present only in the drop area (FIG. 29). This revealed that the mass spectrometry method of the present invention in which platinum vapor deposition is performed is effective for measuring IMS in high spatial resolution mode because the migration effect is reduced.

Example 13

Spray Type Pesticide/Fungicide Agricultural Chemical for Horticulture, Platinum Vapor Deposition A spray type pesticide/fungicide agricultural chemical for horticulture was sprayed onto a leaf of ivy, followed by drying. Platinum nanoparticles were then vapor deposited using a magnetron sputtering device (E-3010: produced by Hitachi Ltd.) to a thickness of 10 nm, thereby preparing a sample. The agricultural chemical that was used contained acetamiprid and thiophanate-methyl as active components.

The sample was measured and analyzed by IMS using a MALDI imaging mass spectrometer (device name: "AutoFlex III" produced by Bruker Corporation).

The measurement conditions of IMS are shown below.
Irradiation laser: Nd:YAG laser (355 nm)
Accelerating voltage: 19 kV
Reflectron voltage: 21 kV
Laser radius: about 100 μm (ultra mode)
Laser intensity: 100%
Measurement interval: 150 μm The results of the analysis of mass spectrum revealed that there was a region where acetamiprid was strongly observed and a region where thiophanate methyl was strongly observed (FIG. 30). Distribution graphs were prepared of a peak at m/z=245 originating from acetamiprid and a peak at m/z=365 originating from thiophanate methyl. The results revealed that acetamiprid was spread in a wide range whereas thiophanate methyl was locally concentrated, indicating that the manner of spreading varied depending on the difference in the agricultural chemical type (FIG. 31). This visually showed that diffusion varies depending on the agricultural chemical type, indicating that the present invention is effective for functional analysis of agricultural chemical formulations.

Example 14

Grain Type Pesticide Agricultural Chemical for Horticulture, Platinum Vapor Deposition A grain type pesticide agricultural chemical for horticulture was scattered on soil in which ivy was planted. 4, 8, 11, and 14 days later, leaves at about 30 mm from the soil were collected, and platinum nanoparticles were vapor deposited using a magnetron sputtering device to a thickness of 10 nm, thereby preparing samples. The grain type agricultural chemical that was used contained acephate as an active component.

Each sample was measured by IMS. Also, for the stems that were collected 4 days later, the lower stem and the upper stem, which were respectively close to and far from the root, were measured by IMS under the same conditions.

The measurement conditions of IMS are shown below.
Irradiation laser: Nd:YAG laser (355 nm)
Accelerating voltage: 19 kV
Reflectron voltage: 21 kV
Laser radius: about 100 μm (ultra mode)
Laser intensity: 100%
Measurement interval: 150 μm The mass spectrum of each of the collected leaves was analyzed. As a result, only the peaks of the wax layer were observed in the range between m/z=400 to 550 for the leaves collected 4 days later, whereas peaks originating from acephate were observed for the leaves collected 11 days later (FIG. 32). A distribution graph of the peak at m/z=206 originating from acephate was prepared, and the results revealed that the distribution of acephate was not observed on the leaves collected 4 days later; however, acephate was observed at the base of the leaves collected 8 days later, and as time passed, i.e., 11 days later and 14 days later, acephate was observed spreading to the tips of the leaves (FIG. 33).

An acephate distribution graph for the stem was also prepared by IMS. As a result, a strong peak of acephate was observed in the lower side of the lower stem close to the soil in which the agricultural chemical was scattered, and a gradual weakening of the acephate peak was observed moving upward along the stem (FIG. 34).

The mass spectrometry method of the present invention in which platinum vapor deposition is performed allows visualization of the permeation and distribution of a scattered agricultural chemical in a plant, and this technique is effective for elucidating the functional mechanism of agricultural chemicals, etc., in plants.

The invention claimed is:

1. A method for imaging mass spectrometry using a sample prepared by physical vapor depositing platinum nanoparticles on a surface of a test sample in such a manner as to bind the platinum nanoparticle to the test sample; the platinum nanoparticles and test sample being subjected to imaging mass spectrometry so as to improve imaging of said test sample.

2. The method according to claim 1, wherein the platinum nanoparticles have an average particle size of 2 to 20 nm.

3. The method according to claim 1, wherein a platinum nanoparticle layer formed by the physical vapor deposition has a thickness of 2 to 50 nm.

4. The method according to claim 1, wherein the physical vapor deposition is based on magnetron sputtering.

5. The method according claim 1 using a matrix assisted laser desorption/ionization (MALDI) imaging mass spectrometer.

6. A method for preparing a sample for imaging mass spectrometry, comprising physical vapor depositing platinum nanoparticles so as to bind the platinum nanoparticles on a surface of a test sample to be subjected to imaging mass spectrometry so as to improve imaging of said test sample.

7. The method according to claim 6, wherein the platinum nanoparticles have an average particle size of 2 to 20 nm.

8. The method according to claim 6, wherein a platinum nanoparticle layer formed by the physical vapor deposition has a thickness of 2 to 50 nm.

9. The method according to claim 6, wherein the physical vapor deposition is based on magnetron sputtering.

* * * * *

UNITED STATES PATENT AND TRADEMARK OFFICE
CERTIFICATE OF CORRECTION

| | | |
|---|---|---|
| PATENT NO. | : 9,355,826 B2 | Page 1 of 1 |
| APPLICATION NO. | : 14/379228 | |
| DATED | : May 31, 2016 | |
| INVENTOR(S) | : Ryuichi Arakawa et al. | |

It is certified that error appears in the above-identified patent and that said Letters Patent is hereby corrected as shown below:

On the title page

Change
Item (22) PCT Filed: "Feb. 13, 2013"

to be

(22) PCT Filed: -- Feb. 15, 2013 --

Signed and Sealed this
Sixteenth Day of August, 2016

Michelle K. Lee
*Director of the United States Patent and Trademark Office*